(12) United States Patent
Caruso et al.

US008283166B2

(10) Patent No.: US 8,283,166 B2
(45) Date of Patent: Oct. 9, 2012

(54) DPH2 GENE DELETION MUTANT AND USES THEREOF

(75) Inventors: Manuel Caruso, Québec (CA); Vincent Roy, Québec (CA)

(73) Assignees: Manuel Caruso, Quebec, Quebec (CA); Vincent Roy, Pierrefonds, Quebec (CA)

( * ) Notice: Subject to any disclaimer, the term of this patent is extended or adjusted under 35 U.S.C. 154(b) by 412 days.

(21) Appl. No.: 12/305,008

(22) PCT Filed: Jun. 18, 2007

(86) PCT No.: PCT/CA2007/001087
§ 371 (c)(1),
(2), (4) Date: Dec. 16, 2008

(87) PCT Pub. No.: WO2007/143858
PCT Pub. Date: Dec. 21, 2007

(65) Prior Publication Data
US 2009/0274670 A1 Nov. 5, 2009

Related U.S. Application Data

(60) Provisional application No. 60/814,049, filed on Jun. 16, 2006.

(51) Int. Cl.
*C12N 5/00* (2006.01)
*A01N 48/00* (2006.01)
*A01N 63/00* (2006.01)

(52) U.S. Cl. .................................. 435/375; 424/93.21

(58) Field of Classification Search ........................ None
See application file for complete search history.

(56) References Cited

U.S. PATENT DOCUMENTS

| 6,440,409 B1 | 8/2002 | Milne et al. |
| 2003/0180756 A1 | 9/2003 | Shi et al. |
| 2005/0287116 A1 | 12/2005 | Rodriguez |

FOREIGN PATENT DOCUMENTS

| WO | 9953762 | 10/1999 |
| WO | 02076437 | 10/2002 |

OTHER PUBLICATIONS

Mattheakis L. C. et al., 1993, "Diphthamide synthesis in *Saccharomyces cerevisiae*: structure of the DPH2 gene", Gene, vol. 132, pp. 149-154.
Liu S. et al., 2004, "Identification of the Proteins Required for Biosynthesis of Diphthamide, the Target of Bacterial ADP-Ribosylating Toxins on Translation Elongation Factor 2", Molecular and Cellular Biology, vol. 24, No. 21, pp. 9487-9497.
Webpage: Roy V. et al., 2006, "*Cricetulus griseus* Dph2 mRNA", National Center for Biotechnology Information, http://www.ncbi.nlm.nih.gov/entrez/viewer.fcgi?115490614:NCBI:15028245, NCBI Sequence Viewer v2.0, 2 pages.
Webpage: Kalnine N. et al., 2003, "*Homo sapiens* diphteria toxin resistance protein required for diphthamide biosynthesis-like 2 (*S. cerevisiae*) mRNA", National Center for Biotechnology Information, http://www.ncbi.nlm.nih.gov/entrez/viewer.fcgi?val=BT007431.1, NCBI Sequence Viewer v2.0, 2 pages.
Qiao J. et al., 2002, "PG13 Packaging Cells Produce Recombinant Retroviruses Carrying a Diphtheria Toxin Mutant Which Kills Cancer Cells", Journal of Virology, vol. 76, No. 14, pp. 7343-7348.
Liu S. et al., 2006, "Dph3, a small protein required for diphtamide biosynthesis, is essential in mouse development.", Mol Cell Biol, vol. 26, pp. 3835-3841.
Chen C. M. et al, 2004, "Ovcal regulates cell proliferation, embryonic development, and tumorigenesis.", Genes Dev, vol. 18, pp. 320-332.
Jorgensen R. et al., 2005, "Exotoxin A-eEF2 complex structure indicates ADP robosylation by robosome mimicry.", Nature, vol. 436, pp. 979-984.

*Primary Examiner* — Ram R. Shukla
*Assistant Examiner* — Khatol Shahnan-Shah
(74) *Attorney, Agent, or Firm* — Norton Rose Canada LLP

(57) ABSTRACT

Diphtheria and *Pseudomonas* infections are very common worldwide. The toxins involved in the pathogenesis of those diseases act by inactivating the elongation factor-2 (EF-2), therefore blocking protein synthesis and leading to cell death. Diphthamide formation on EF-2 is a prerequisite step in the inactivation of EF-2, and Dph proteins have been identified as modulating this process. The present application concerns Dph2 deletion mutant genes and proteins and their uses in vitro and in vivo.

1 Claim, 8 Drawing Sheets

Dph2 (489aa)

Dph2(C-) (398aa)

SEQUENCE LISTING

<160> NUMBER OF SEQ ID NOS: 21

<210> SEQ ID NO 1
<211> LENGTH: 1470
<212> TYPE: DNA
<213> ORGANISM: Hamster sp.

<400> SEQUENCE: 1

```
atggagtcta cgttcagcag ccccgcggag gcggccttac agcgggaggc gggcgtccca      60
ggactgttca cccctcccga agacctcgac cgagtgtacg agctggagcg agtcacgaaa     120
tttgtctgcg atttggggtg tcagcgggtg gccttacagt tccctgacca attactggga     180
gatgccggag cagtggctgt aaggctggag gaagtcacag gatctaagat gttcatttta     240
ggggacacgg cttatggcag ctgctgtgtg gatgtgctgg gtgctgagca ggctggagct     300
gaagcccttg ttcactttgg tcctgcctgc ttaagccccc ctgccagcct gctgccgatc     360
accttcgtcc ttggtcagcg ttctgttgcc ctagagctct gtgcgaaggc ctttgaagcc     420
cggaacccag atcccacagc accggtggta ctgctgagtg agccagcttg tgcccatgcc     480
ctagaggctt tggccactct gctgcgccca aagtaccaag atctgctcat ctccagccca     540
gctcttcccc tgccagtggg gtccccaagt tcacagcctg agcctctgga gcgtttgga     600 cgacgcttcc ccctgagccc aggaaggtgt ctggaagaat atggtgcctt ctatgtgggc     660
ggttctcaag ccagctctga ccctgtcctt gatccagatc tgagcagact gctcttgggt     720
tggacaccgg gacgacccctt catttcctgc tgtccagaca caggacagac acaagaccag     780
ggtgtccagg ctgggcggct aagagcacga agactgtatc ttatagagag ggccagagat     840
gcccatgtag tagggctgct ggcaggcaca ttaggcgtag ctcaacaccg tgaggcactg     900
```

```
gcacacttac ggaaactgac tgaggctgct ggaaaacgta gctatgtact ggccctgggg    960
aggcccacac ctgccaagct tgccaacttc cctgagatgg acatctttgt gcttttggcc   1020
tgtccgctgg gagccctagc ccccagcct tcaggtggct tctttcggcc catattgaca    1080
ccatgtgaat tggaggctgc ctgtaaccct gcctggccac ctccaggcct ggctccccac   1140
ctcacacatt atgcagagct gttgcctggt tctccctttt atgttccact cccaccccct   1200
gagtcagaat tgtgggatac cccagatgtg tcgctcattt ctggagacct ccgaccacca   1260
ccttcttgga agtcatccag tgacactggg tgttctgccc taactccaag gccccagctg   1320
gagctagctg agagcagccc tgcagcttca ttccttagtt cccggagctg cagggatta    1380 gagccccgct tgggccagac accagtgaaa gaagctgtcc aaggaagacg aggtattgcc   1440
attgcctatg aggatgaggg cagcggctga                                     1470
```

<210> SEQ ID NO 2
<211> LENGTH: 489
<212> TYPE: PRT
<213> ORGANISM: Hamster sp.

<400> SEQUENCE: 2

```
Met Glu Ser Thr Phe Ser Ser Pro Ala Glu Ala Leu Gln Arg Glu
1               5                  10                  15

Ala Gly Val Pro Gly Leu Phe Thr Pro Pro Glu Asp Leu Asp Arg Val
            20                  25                  30

Tyr Glu Leu Glu Arg Val Thr Lys Phe Val Cys Asp Leu Gly Cys Gln
        35                  40                  45

Arg Val Ala Leu Gln Phe Pro Asp Gln Leu Leu Gly Asp Ala Gly Ala
    50                  55                  60

Val Ala Val Arg Leu Glu Glu Val Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Glu Ala Leu Val His Phe Gly Pro Ala Cys Leu Ser
            100                 105                 110

Pro Pro Ala Ser Leu Leu Pro Ile Thr Phe Val Leu Gly Gln Arg Ser
        115                 120                 125

Val Ala Leu Glu Leu Cys Ala Lys Ala Phe Glu Ala Arg Asn Pro Asp
    130                 135                 140

Pro Thr Ala Pro Val Val Leu Leu Ser Glu Pro Ala Cys Ala His Ala
145                 150                 155                 160

Leu Glu Ala Leu Ala Thr Leu Leu Arg Pro Lys Tyr Gln Asp Leu Leu
                165                 170                 175

Ile Ser Ser Pro Ala Leu Pro Leu Pro Val Gly Ser Pro Ser Ser Gln
            180                 185                 190

Pro Glu Pro Leu Glu Arg Phe Gly Arg Arg Phe Pro Leu Ser Pro Gly
        195                 200                 205

Arg Cys Leu Glu Glu Tyr Gly Ala Phe Tyr Val Gly Gly Ser Gln Ala
    210                 215                 220

Ser Ser Asp Pro Val Leu Asp Pro Asp Leu Ser Arg Leu Leu Leu Gly
225                 230                 235                 240

Trp Thr Pro Gly Arg Pro Phe Ile Ser Cys Cys Pro Thr Gly Gln
                245                 250                 255

Thr Gln Asp Gln Gly Val Gln Ala Gly Arg Leu Arg Ala Arg Arg Leu
            260                 265                 270

Tyr Leu Ile Glu Arg Ala Arg Asp Ala His Val Val Gly Leu Leu Ala
```

```
                    275                 280                 285
Gly Thr Leu Gly Val Ala Gln His Arg Glu Ala Leu Ala His Leu Arg
            290                 295                 300
Lys Leu Thr Glu Ala Ala Gly Lys Arg Ser Tyr Val Leu Ala Leu Gly
305                 310                 315                 320
Arg Pro Thr Pro Ala Lys Leu Ala Asn Phe Pro Glu Met Asp Ile Phe
                325                 330                 335
Val Leu Leu Ala Cys Pro Leu Gly Ala Leu Ala Pro Gln Pro Ser Gly
                    340                 345                 350
Gly Phe Phe Arg Pro Ile Leu Thr Pro Cys Glu Leu Glu Ala Ala Cys
            355                 360                 365
Asn Pro Ala Trp Pro Pro Gly Leu Ala Pro His Leu Thr His Tyr
        370                 375                 380
Ala Glu Leu Leu Pro Gly Ser Pro Phe Tyr Val Pro Leu Pro Pro Pro
385                 390                 395                 400
Glu Ser Glu Leu Trp Asp Thr Pro Asp Val Ser Leu Ile Ser Gly Asp
                    405                 410                 415
Leu Arg Pro Pro Ser Trp Lys Ser Ser Ser Asp Thr Gly Cys Ser
            420                 425                 430
Ala Leu Thr Pro Arg Pro Gln Leu Glu Leu Ala Glu Ser Ser Pro Ala
435                 440                 445
Ala Ser Phe Leu Ser Ser Arg Ser Trp Gln Gly Leu Glu Pro Arg Leu
                    450                 455                 460
Gly Gln Thr Pro Val Lys Glu Ala Val Gln Gly Arg Arg Gly Ile Ala
465                 470                 475                 480
Ile Ala Tyr Glu Asp Glu Gly Ser Gly
                485

<210> SEQ ID NO 3
<211> LENGTH: 1215
<212> TYPE: DNA
<213> ORGANISM: Hamster sp.
<220> FEATURE:
<221> NAME/KEY: misc_feature
<222> LOCATION: (1195)..(1215)
<223> OTHER INFORMATION: vector-originating sequence

<400> SEQUENCE: 3
atggagtcta cgttcagcag ccccgcggag gcggccttac agcgggaggc gggcgtccca      60
ggactgttca cccctcccga agacctcgac cgagtgtacg agctggagcg agtcacgaaa     120
tttgtctgcg atttggggtg tcagcgggtg gccttacagt tccctgacca attactggga     180
gatgccggag cagtggctgt aaggctggag gaagtcacag gatctaagat gttcatttta     240
ggggacacgg cttatggcag ctgctgtgtg gatgtgctgg gtgctgagca ggctggagct     300
gaagcccttg ttcactttgg tcctgcctgc ttaagccccc ctgccagcct gctgccgatc     360
accttcgtcc ttggtcagcg ttctgttgcc ctagagctct gtgcgaaggc cttttgaagcc     420 cggaacccag atcccacagc accggtggta ctgctgagtg agccagcttg tgcccatgcc     480
ctagaggctt tggccactct gctgcgccca aagtaccaag atctgctcat ctccagccca     540
gctcttcccc tgccagtggg gtccccaagt tcacagcctg agcctctgga gcgttttgga     600
cgacgcttcc ccctgagccc aggaaggtgt ctggaagaat atggtgcctt ctatgtgggc     660
ggttctcaag ccagctctga ccctgtcctt gatccagatc tgagcagact gctcttgggt     720
tggacaccgg gacgacccctt catttcctgc tgtccagaca caggacagac acaagaccag     780
ggtgtccagg ctgggcggct aagagcacga agactgtatc ttatagagag ggccagagat     840
```

-continued

```
gcccatgtag tagggctgct ggcaggcaca ttaggcgtag ctcaacaccg tgaggcactg      900
gcacacttac ggaaactgac tgaggctgct ggaaaacgta gctatgtact ggccctgggg      960
aggcccacac ctgccaagct tgccaacttc cctgagatgg acatctttgt gcttttggcc     1020
tgtccgctgg gagccctagc ccccagcct tcaggtggct tctttcggcc catattgaca     1080
ccatgtgaat tggaggctgc ctgtaaccct gcctggccac ctccaggcct ggctccccac     1140
ctcacacatt atgcagagct gttgcctggt tctcccttt atgttccact cccgaattcg     1200
gatccagatc cctga                                                     1215
```

<210> SEQ ID NO 4
<211> LENGTH: 404
<212> TYPE: PRT
<213> ORGANISM: Hamster sp.
<220> FEATURE:
<221> NAME/KEY: MISC_FEATURE
<222> LOCATION: (399)..(404)
<223> OTHER INFORMATION: vector-originating sequence

<400> SEQUENCE: 4

```
Met Glu Ser Thr Phe Ser Ser Pro Ala Glu Ala Leu Gln Arg Glu
1               5                   10                  15

Ala Gly Val Pro Gly Leu Phe Thr Pro Pro Glu Asp Leu Asp Arg Val
                20                  25                  30

Tyr Glu Leu Glu Arg Val Thr Lys Phe Val Cys Asp Leu Gly Cys Gln
            35                  40                  45

Arg Val Ala Leu Gln Phe Pro Asp Gln Leu Leu Gly Asp Ala Gly Ala
        50                  55                  60

Val Ala Val Arg Leu Glu Glu Val Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Glu Ala Leu Val His Phe Gly Pro Ala Cys Leu Ser
            100                 105                 110

Pro Pro Ala Ser Leu Leu Pro Ile Thr Phe Val Leu Gly Gln Arg Ser
        115                 120                 125

Val Ala Leu Glu Leu Cys Ala Lys Ala Phe Glu Ala Arg Asn Pro Asp
130                 135                 140

Pro Thr Ala Pro Val Val Leu Leu Ser Glu Pro Ala Cys Ala His Ala
145                 150                 155                 160

Leu Glu Ala Leu Ala Thr Leu Leu Arg Pro Lys Tyr Gln Asp Leu Leu
                165                 170                 175

Ile Ser Ser Pro Ala Leu Pro Leu Pro Val Gly Ser Pro Ser Ser Gln
            180                 185                 190

Pro Glu Pro Leu Glu Arg Phe Gly Arg Arg Phe Pro Leu Ser Pro Gly
        195                 200                 205

Arg Cys Leu Glu Glu Tyr Gly Ala Phe Tyr Val Gly Gly Ser Gln Ala
    210                 215                 220

Ser Ser Asp Pro Val Leu Asp Pro Asp Leu Ser Arg Leu Leu Leu Gly
225                 230                 235                 240

Trp Thr Pro Gly Arg Pro Phe Ile Ser Cys Cys Pro Asp Thr Gly Gln
                245                 250                 255

Thr Gln Asp Gln Gly Val Gln Ala Gly Arg Leu Arg Ala Arg Arg Leu
            260                 265                 270

Tyr Leu Ile Glu Arg Ala Arg Asp Ala His Val Val Gly Leu Leu Ala
        275                 280                 285
```

Gly Thr Leu Gly Val Ala Gln His Arg Glu Ala Leu Ala His Leu Arg
            290                 295                 300

Lys Leu Thr Glu Ala Ala Gly Lys Arg Ser Tyr Val Leu Ala Leu Gly
305                 310                 315                 320

Arg Pro Thr Pro Ala Lys Leu Ala Asn Phe Pro Glu Met Asp Ile Phe
                325                 330                 335

Val Leu Leu Ala Cys Pro Leu Gly Ala Leu Ala Pro Gln Pro Ser Gly
            340                 345                 350

Gly Phe Phe Arg Pro Ile Leu Thr Pro Cys Glu Leu Glu Ala Ala Cys
        355                 360                 365

Asn Pro Ala Trp Pro Pro Gly Leu Ala Pro His Leu Thr His Tyr
    370                 375                 380

Ala Glu Leu Leu Pro Gly Ser Pro Phe Tyr Val Pro Leu Pro Asn Ser
385                 390                 395                 400

Asp Pro Asp Pro

<210> SEQ ID NO 5
<211> LENGTH: 1200
<212> TYPE: DNA
<213> ORGANISM: Hamster sp.
<220> FEATURE:
<221> NAME/KEY: misc_feature
<222> LOCATION: (1195)..(1200)
<223> OTHER INFORMATION: vector-originating sequence

<400> SEQUENCE: 5

```
atggagtcta cgttcagcag ccccgcggag gcggccttac agcgggaggc gggcgtccca      60
ggactgttca cccctcccga agacctcgac cgagtgtacg agctggagcg agtcacgaaa     120
tttgtctgcg atttggggtg tcagcggtg gccttacagt tccctgacca attactggga     180
gatgccggag cagtggctgt aaggctggag gaagtcacag gatctaagat gttcatttta     240
ggggacacgg cttatggcag ctgctgtgtg gatgtgctgg gtgctgagca ggctggagct     300
gaagcccttg ttcactttgg tcctgcctgc ttaagccccc ctgccagcct gctgccgatc     360
accttcgtcc ttggtcagcg ttctgttgcc ctagagctct gtgcgaaggc ctttgaagcc     420
cggaacccag atcccacagc accggtggta ctgctgagtg agccagcttg tgcccatgcc     480
ctagaggctt tggccactct gctgcgccca aagtaccaag atctgctcat ctccagccca     540
gctcttcccc tgccagtggg gtccccaagt tcacagcctg agcctctgga gcgttttgga     600
cgacgcttcc ccctgagccc aggaaggtgt ctggaagaat atggtgcctt ctatgtgggc     660
ggttctcaag ccagctctga ccctgtcctt gatccagatc tgagcagact gctcttgggt     720
tggacaccgg gacgacccct cattcctgc tgtccagaca caggacagac acaagaccag     780
ggtgtccagg ctgggcggct aagagcacga agactgtatc ttatagagag ggccagagat     840
gcccatgtag tagggctgct ggcaggcaca ttaggcgtag ctcaacaccg tgaggcactg     900
gcacacttac ggaaactgac tgaggctgct ggaaaacgta gctatgtact ggccctgggg     960
aggcccacac ctgccaagct tgccaacttc cctgagatgg acatctttgt gcttttggcc    1020
tgtccgctgg gagccctagc ccccagcct tcaggtggct tctttcggcc catattgaca    1080
ccatgtgaat tggaggctgc ctgtaaccct gcctggccac ctccaggcct ggctccccac    1140
ctcacacatt atgcagagct gttgcctggt tctccctttt atgttccact cccgaattaa    1200
```

<210> SEQ ID NO 6
<211> LENGTH: 399
<212> TYPE: PRT

```
<213> ORGANISM: Hamster sp.
<220> FEATURE:
<221> NAME/KEY: MISC_FEATURE
<222> LOCATION: (399)..(399)
<223> OTHER INFORMATION: vector-originating residue

<400> SEQUENCE: 6
```

Met Glu Ser Thr Phe Ser Ser Pro Ala Glu Ala Leu Gln Arg Glu
1               5                   10                  15

Ala Gly Val Pro Gly Leu Phe Thr Pro Pro Glu Asp Leu Asp Arg Val
            20                  25                  30

Tyr Glu Leu Glu Arg Val Thr Lys Phe Val Cys Asp Leu Gly Cys Gln
            35                  40                  45

Arg Val Ala Leu Gln Phe Pro Asp Gln Leu Leu Gly Asp Ala Gly Ala
50                  55                  60

Val Ala Val Arg Leu Glu Glu Val Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Glu Ala Leu Val His Phe Gly Pro Ala Cys Leu Ser
            100                 105                 110

Pro Pro Ala Ser Leu Leu Pro Ile Thr Phe Val Leu Gly Gln Arg Ser
            115                 120                 125

Val Ala Leu Glu Leu Cys Ala Lys Ala Phe Glu Ala Arg Asn Pro Asp
130                 135                 140

Pro Thr Ala Pro Val Val Leu Ser Glu Pro Ala Cys Ala His Ala
145                 150                 155                 160

Leu Glu Ala Leu Ala Thr Leu Leu Arg Pro Lys Tyr Gln Asp Leu Leu
                165                 170                 175

Ile Ser Ser Pro Ala Leu Pro Leu Pro Val Gly Ser Pro Ser Ser Gln
            180                 185                 190

Pro Glu Pro Leu Glu Arg Phe Gly Arg Arg Phe Pro Leu Ser Pro Gly
            195                 200                 205

Arg Cys Leu Glu Glu Tyr Gly Ala Phe Tyr Val Gly Gly Ser Gln Ala
210                 215                 220

Ser Ser Asp Pro Val Leu Asp Pro Asp Leu Ser Arg Leu Leu Leu Gly
225                 230                 235                 240

Trp Thr Pro Gly Arg Pro Phe Ile Ser Cys Cys Pro Asp Thr Gly Gln
                245                 250                 255

Thr Gln Asp Gln Gly Val Gln Ala Gly Arg Leu Arg Ala Arg Arg Leu
            260                 265                 270

Tyr Leu Ile Glu Arg Ala Arg Asp Ala His Val Val Gly Leu Leu Ala
            275                 280                 285

Gly Thr Leu Gly Val Ala Gln His Arg Glu Ala Leu Ala His Leu Arg
290                 295                 300

Lys Leu Thr Glu Ala Ala Gly Lys Arg Ser Tyr Val Leu Ala Leu Gly
305                 310                 315                 320

Arg Pro Thr Pro Ala Lys Leu Ala Asn Phe Pro Glu Met Asp Ile Phe
                325                 330                 335

Val Leu Leu Ala Cys Pro Leu Gly Ala Leu Ala Pro Gln Pro Ser Gly
            340                 345                 350

Gly Phe Phe Arg Pro Ile Leu Thr Pro Cys Glu Leu Glu Ala Ala Cys
            355                 360                 365

Asn Pro Ala Trp Pro Pro Gly Leu Ala Pro His Leu Thr His Tyr
370                 375                 380

```
Ala Glu Leu Leu Pro Gly Ser Pro Phe Tyr Val Pro Leu Pro Asn
385                 390                 395
```

<210> SEQ ID NO 7
<211> LENGTH: 1470
<212> TYPE: DNA
<213> ORGANISM: Homo sapiens

<400> SEQUENCE: 7

```
atggagtcga tgtttagcag ccctgccgag gcggcgctgc agcgagagac cggggtgcca      60
ggactgctta ctcctcttcc ggacctggac ggagtgtacg agctggagcg agtcgctgga     120
tttgtccgcg acctggggtg tgaacgagtt gccttgcagt tccctgacca gctattggga     180
gatgctgtgg ctgtggctgc acgactggag gagacgacag ggtcaaagat gttcattctg     240
ggtgacacag cctacggcag ctgctgcgtg gatgtgctgg gtgctgagca agctggagct     300
caggctctca tacattttgg ccctgcctgc ttaagccctc agcccgccc actgcccgtt      360
gccttcgtgc ttcgtcaacg ttctgtggcc ttggagctct gtgtcaaggc ctttgaggcc     420
cagaacccag accccaaagc cctgtggtg ctgctgagtg agccggcctg tgcccatgcc      480
ctggaggctt tggctactct cctgcgccca cggtacctgg acctgctagt ctccagccca     540
gcttttcccc aaccagtggg ttccctgagt ccagagccta tgccctaga gcgttttggg      600
cgccgcttcc cccttgcccc agggaggcgt ctagaagagt atggtgcctt ctatgtaggg     660
ggctctaagg ccagccctga cccagacctt gacccagacc tgagtcggct gctcttgggg     720
tgggcaccag gtcaaccctt ctcctcctgc tgtccagata cagggaagac tcaggatgag     780
ggtgcccggg ctggacggct aagggcacga agacgatatc tggtagagag ggccagagat     840
gcccgcgtgg tagggctgct ggcaggcaca ctgggtgtag cccaacaccg tgaggcactg     900
gcccacttgc ggaacctgac tcaggctgct ggcaagcgta gctatgtgtt ggccctgggg     960
cggcccaccc ctgccaagct tgccaacttc cctgaggtgg atgtctttgt gctattagcc    1020
tgtcctctgg gtgctctagc cccccagctt tctggtagct tcttccagcc tatactggca    1080
ccatgtgagc tggaagctgc ctgcaaccct gcctggccac ctccaggcct ggctcccccac   1140
ctcacacatt atgcggactt attgcctggc tctcccttcc acgtggctct cccaccacct    1200
gagtcagagc tgtgggaaac cccagacgtg tcactcatta ctggagatct ccgaccccca    1260
cctgcctgga agtcatcaaa tgatcatgga agcttggctc tgaccccacg gccccagctg    1320
gagctggctg agagcagtcc tgcagcctca ttccttagtt cccggagctg gcaagggctg    1380
gagccccgcc tgggtcagac gccagtgaca gaagctgtga gtggaagacg agggattgcc    1440
atcgcctatg aggatgaggg aagcggctga                                     1470
```

<210> SEQ ID NO 8
<211> LENGTH: 489
<212> TYPE: PRT
<213> ORGANISM: Homo sapiens

<400> SEQUENCE: 8

```
Met Glu Ser Met Phe Ser Ser Pro Ala Glu Ala Leu Gln Arg Glu
1               5                   10                  15

Thr Gly Val Pro Gly Leu Leu Thr Pro Leu Pro Asp Leu Asp Gly Val
            20                  25                  30

Tyr Glu Leu Glu Arg Val Ala Gly Phe Val Arg Asp Leu Gly Cys Glu
        35                  40                  45

Arg Val Ala Leu Gln Phe Pro Asp Gln Leu Leu Gly Asp Ala Val Ala
    50                  55                  60
```

```
Val Ala Ala Arg Leu Glu Glu Thr Thr Gly Ser Lys Met Phe Ile Leu
 65                  70                  75                  80

Gly Asp Thr Ala Tyr Gly Ser Cys Cys Val Asp Val Leu Gly Ala Glu
                 85                  90                  95

Gln Ala Gly Ala Gln Ala Leu Ile His Phe Gly Pro Ala Cys Leu Ser
            100                 105                 110

Pro Pro Ala Arg Pro Leu Pro Val Ala Phe Val Leu Arg Gln Arg Ser
            115                 120                 125

Val Ala Leu Glu Leu Cys Val Lys Ala Phe Glu Ala Gln Asn Pro Asp
130                 135                 140

Pro Lys Ala Pro Val Val Leu Leu Ser Glu Pro Ala Cys Ala His Ala
145                 150                 155                 160

Leu Glu Ala Leu Ala Thr Leu Leu Arg Pro Arg Tyr Leu Asp Leu Leu
                165                 170                 175

Val Ser Ser Pro Ala Phe Pro Gln Pro Val Gly Ser Leu Ser Pro Glu
            180                 185                 190

Pro Met Pro Leu Glu Arg Phe Gly Arg Arg Phe Pro Leu Ala Pro Gly
        195                 200                 205

Arg Arg Leu Glu Glu Tyr Gly Ala Phe Tyr Val Gly Gly Ser Lys Ala
210                 215                 220

Ser Pro Asp Pro Asp Leu Asp Pro Asp Leu Ser Arg Leu Leu Leu Gly
225                 230                 235                 240

Trp Ala Pro Gly Gln Pro Phe Ser Ser Cys Cys Pro Asp Thr Gly Lys
                245                 250                 255

Thr Gln Asp Glu Gly Ala Arg Ala Gly Arg Leu Arg Ala Arg Arg Arg
            260                 265                 270

Tyr Leu Val Glu Arg Ala Arg Asp Ala Arg Val Val Gly Leu Leu Ala
            275                 280                 285

Gly Thr Leu Gly Val Ala Gln His Arg Glu Ala Leu Ala His Leu Arg
        290                 295                 300

Asn Leu Thr Gln Ala Ala Gly Lys Arg Ser Tyr Val Leu Ala Leu Gly
305                 310                 315                 320

Arg Pro Thr Pro Ala Lys Leu Ala Asn Phe Pro Glu Val Asp Val Phe
                325                 330                 335

Val Leu Leu Ala Cys Pro Leu Gly Ala Leu Ala Pro Gln Leu Ser Gly
            340                 345                 350

Ser Phe Phe Gln Pro Ile Leu Ala Pro Cys Glu Leu Glu Ala Ala Cys
            355                 360                 365

Asn Pro Ala Trp Pro Pro Gly Leu Ala Pro His Leu Thr His Tyr
370                 375                 380

Ala Asp Leu Leu Pro Gly Ser Pro Phe His Val Ala Leu Pro Pro Pro
385                 390                 395                 400

Glu Ser Glu Leu Trp Glu Thr Pro Asp Val Ser Leu Ile Thr Gly Asp
                405                 410                 415

Leu Arg Pro Pro Ala Trp Lys Ser Ser Asn Asp His Gly Ser Leu
            420                 425                 430

Ala Leu Thr Pro Arg Pro Gln Leu Glu Leu Ala Glu Ser Ser Pro Ala
        435                 440                 445

Ala Ser Phe Leu Ser Ser Arg Ser Trp Gln Gly Leu Glu Pro Arg Leu
            450                 455                 460

Gly Gln Thr Pro Val Thr Glu Ala Val Ser Gly Arg Arg Gly Ile Ala
465                 470                 475                 480

Ile Ala Tyr Glu Asp Glu Gly Ser Gly
```

<210> SEQ ID NO 9
<211> LENGTH: 1197
<212> TYPE: DNA
<213> ORGANISM: Homo sapiens

<400> SEQUENCE: 9

| | | | | | |
|---|---|---|---|---|---|
| atggagtcga | tgtttagcag | ccctgccgag | gcggcgctgc | agcgagagac | cggggtgcca | 60 |
| ggactgctta | ctcctcttcc | ggacctggac | ggagtgtacg | agctggagcg | agtcgctgga | 120 |
| tttgtccgcg | acctggggtg | tgaacgagtt | gccttgcagt | tccctgacca | gctattggga | 180 |
| gatgctgtgg | ctgtggctgc | acgactggag | gagacgacag | ggtcaaagat | gttcattctg | 240 |
| ggtgacacag | cctacggcag | ctgctgcgtg | gatgtgctgg | gtgctgagca | agctggagct | 300 |
| caggctctca | tacattttgg | ccctgcctgc | ttaagccctc | cagcccgccc | actgccgtt | 360 |
| gccttcgtgc | ttcgtcaacg | ttctgtggcc | ttggagctct | gtgtcaaggc | ctttgaggcc | 420 |
| cagaacccag | accccaaagc | gcctgtggtg | ctgctgagtg | agccggcctg | tgcccatgcc | 480 |
| ctggaggctt | tggctactct | cctgcgccca | cggtacctgg | acctgctagt | ctccagccca | 540 |
| gcttttcccc | aaccagtggg | ttccctgagt | ccagagccta | tgcccctaga | gcgttttggg | 600 |
| cgccgcttcc | cccttgcccc | agggaggcgt | ctagaagagt | atggtgcctt | ctatgtaggg | 660 |
| ggctctaagg | ccagccctga | cccagacctt | gacccagacc | tgagtcggct | gctcttgggg | 720 |
| tgggcaccag | gtcaacccct | tcctcctgc | tgtccagata | cagggaagac | tcaggatgag | 780 |
| ggtgcccggg | ctggacggct | aagggcacga | agacgatatc | tggtagagag | ggccagagat | 840 |
| gcccgcgtgg | tagggctgct | ggcaggcaca | ctgggtgtag | cccaacaccg | tgaggcactg | 900 |
| gcccacttgc | ggaacctgac | tcaggctgct | ggcaagcgta | gctatgtgtt | ggccctgggg | 960 |
| cggcccaccc | ctgccaagct | tgccaacttc | cctgaggtgg | atgtctttgt | gctattagcc | 1020 |
| tgtcctctgg | gtgctctagc | cccccagctt | tctggtagct | tcttccagcc | tatactggca | 1080 |
| ccatgtgagc | tggaagctgc | ctgcaaccct | gcctggccac | ctccaggcct | ggctccccac | 1140 |
| ctcacacatt | atgcggactt | attgcctggc | tctcccttcc | acgtggctct | cccatga | 1197 |

<210> SEQ ID NO 10
<211> LENGTH: 398
<212> TYPE: PRT
<213> ORGANISM: Homo sapiens

<400> SEQUENCE: 10

Met Glu Ser Met Phe Ser Ser Pro Ala Glu Ala Ala Leu Gln Arg Glu
1               5                   10                  15

Thr Gly Val Pro Gly Leu Leu Thr Pro Leu Pro Asp Leu Asp Gly Val
            20                  25                  30

Tyr Glu Leu Glu Arg Val Ala Gly Phe Val Arg Asp Leu Gly Cys Glu
        35                  40                  45

Arg Val Ala Leu Gln Phe Pro Asp Gln Leu Leu Gly Asp Ala Val Ala
    50                  55                  60

Val Ala Ala Arg Leu Glu Glu Thr Thr Gly Ser Lys Met Phe Ile Leu
65                  70                  75                  80

Gly Asp Thr Ala Tyr Gly Ser Cys Cys Val Asp Val Leu Gly Ala Glu
                85                  90                  95

Gln Ala Gly Ala Gln Ala Leu Ile His Phe Gly Pro Ala Cys Leu Ser
            100                 105                 110

Pro Pro Ala Arg Pro Leu Pro Val Ala Phe Val Leu Arg Gln Arg Ser

```
              115                 120                 125
Val Ala Leu Glu Leu Cys Val Lys Ala Phe Glu Ala Gln Asn Pro Asp
130                 135                 140

Pro Lys Ala Pro Val Val Leu Leu Ser Glu Pro Ala Cys Ala His Ala
145                 150                 155                 160

Leu Glu Ala Leu Ala Thr Leu Arg Pro Arg Tyr Leu Asp Leu Leu
                165                 170                 175

Val Ser Ser Pro Ala Phe Pro Gln Pro Val Gly Ser Leu Ser Pro Glu
                180                 185                 190

Pro Met Pro Leu Glu Arg Phe Gly Arg Phe Pro Leu Ala Pro Gly
                195                 200                 205

Arg Arg Leu Glu Glu Tyr Gly Ala Phe Tyr Val Gly Gly Ser Lys Ala
                210                 215                 220

Ser Pro Asp Pro Asp Leu Asp Pro Asp Leu Ser Arg Leu Leu Leu Gly
225                 230                 235                 240

Trp Ala Pro Gly Gln Pro Phe Ser Ser Cys Cys Pro Asp Thr Gly Lys
                245                 250                 255

Thr Gln Asp Glu Gly Ala Arg Ala Gly Arg Leu Arg Ala Arg Arg Arg
                260                 265                 270

Tyr Leu Val Glu Arg Ala Arg Asp Ala Arg Val Val Gly Leu Leu Ala
                275                 280                 285

Gly Thr Leu Gly Val Ala Gln His Arg Glu Ala Leu Ala His Leu Arg
                290                 295                 300

Asn Leu Thr Gln Ala Ala Gly Lys Arg Ser Tyr Val Leu Ala Leu Gly
305                 310                 315                 320

Arg Pro Thr Pro Ala Lys Leu Ala Asn Phe Pro Glu Val Asp Val Phe
                325                 330                 335

Val Leu Leu Ala Cys Pro Leu Gly Ala Leu Ala Pro Gln Leu Ser Gly
                340                 345                 350

Ser Phe Phe Gln Pro Ile Leu Ala Pro Cys Glu Leu Glu Ala Ala Cys
                355                 360                 365

Asn Pro Ala Trp Pro Pro Gly Leu Ala Pro His Leu Thr His Tyr
370                 375                 380

Ala Asp Leu Leu Pro Gly Ser Pro Phe His Val Ala Leu Pro
385                 390                 395

<210> SEQ ID NO 11
<211> LENGTH: 29
<212> TYPE: DNA
<213> ORGANISM: Artificial
<220> FEATURE:
<223> OTHER INFORMATION: primer

<400> SEQUENCE: 11
atcgaattca tggagtctac gttcagcag                                    29

<210> SEQ ID NO 12
<211> LENGTH: 18
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
```

<400> SEQUENCE: 12
tcagcngctn ccctcatc                                          18

<210> SEQ ID NO 13
<211> LENGTH: 26
<212> TYPE: DNA
<213> ORGANISM: Artificial
<220> FEATURE:
<223> OTHER INFORMATION: primer

<400> SEQUENCE: 13
cggggtacca tggagtctac gttcag                                 26

<210> SEQ ID NO 14
<211> LENGTH: 26
<212> TYPE: DNA
<213> ORGANISM: Artificial
<220> FEATURE:
<223> OTHER INFORMATION: primer

<400> SEQUENCE: 14
cgcggatccg ccgctgccct catcct                                 26

<210> SEQ ID NO 15
<211> LENGTH: 20
<212> TYPE: DNA
<213> ORGANISM: Artificial
<220> FEATURE:
<223> OTHER INFORMATION: primer

<400> SEQUENCE: 15
gaattcggga gtggaacata                                        20

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
ttaattcggg agtggaacat                                        20

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
cgcggtacca tggagccagc ttgtgc                                 26

<210> SEQ ID NO 18
<211> LENGTH: 17
<212> TYPE: DNA
<213> ORGANISM: Artificial
<220> FEATURE:
<223> OTHER INFORMATION: primer

<400> SEQUENCE: 18
ggcatgggca caagctg                                           17

<210> SEQ ID NO 19
<211> LENGTH: 18

-continued

```
<212> TYPE: DNA
<213> ORGANISM: Artificial
<220> FEATURE:
<223> OTHER INFORMATION: primer

<400> SEQUENCE: 19
atctccagcc cagctctt                                                    18

<210> SEQ ID NO 20
<211> LENGTH: 15
<212> TYPE: DNA
<213> ORGANISM: Artificial
<220> FEATURE:
<223> OTHER INFORMATION: primer

<400> SEQUENCE: 20
atggcggcgc tggta                                                       15

<210> SEQ ID NO 21
<211> LENGTH: 25
<212> TYPE: DNA
<213> ORGANISM: Artificial
<220> FEATURE:
<223> OTHER INFORMATION: primer

<400> SEQUENCE: 21
cgcggatccg ggagccggcg aagta                                            25
```

DPH2 GENE DELETION MUTANT AND USES THEREOF

CROSS-REFERENCE TO RELATED APPLICATIONS

Figure 1:

This application claims priority from U.S. provisional application 60/814,049 filed Jun. 16, 2006.

BACKGROUND OF THE INVENTION

Infections by *Pseudomonas aeruginosa* and *Corynebacterium diphtheria* are still very common worldwide. Diphtheria infections are still endemic in several regions, including Africa, India, Bangladesh, Vietnam, South America and Russia, and cases are reported all over the world. Recent outbreaks of diphtheria have also been reported in countries like the Newly Independent States of the former Soviet Union, and in poor, socio-economically disadvantaged groups living in crowded conditions of Europe and the United States. Diphtheria infections are still the cause of numbers of deaths in the world, and are still important despite the vast vaccination programs against this pathogen. The re-emergence of epidemic in countries where vaccinations and immunizations have been performed could be explained by the introduction of a new biotype of toxigenic *C. diphtheria* and a large gap of immunity among adults. In fact, it is well known that the level of immunity declines in late childhood and adolescence, and some serological surveys demonstrated that 20% to >50% of adolescents and adults lack immunity to diphtheria toxin in the US. Even when properly treated, between 5%-10% of diphtheria patients will die from this infection.

*P. aeruginosa* is a Gram-negative *bacillus* ubiquitously present in the environment and, according to the Centers for Disease Control and Prevention, the fourth most commonly isolated nosocomial pathogen. Nearly all *P. aeruginosa* clinical cases are associated with compromised host defense. Systemic infections are also common in patients with severe burns, and in immunosuppressed AIDS and cancer patients. The infection by *P. aeruginosa* can also be seen with contact lenses wearers that develop keratitis of the cornea. In addition, *P. aeruginosa* is responsible for ventilator-acquired pneumonia, and it is the primary cause of mortality in cystic fibrosis patients due to lung infection.

It is well known that the diphtheria toxin (DT) is the virulence factor of *C. diphtheria*, and that exotoxin A (ETA) is one of the many virulence factors of *P. aeruginosa*, and it has been shown to be produced by 95% of *P. aeruginosa* clinical isolates. It has been reported that ETA deficient strains are twenty times less virulent in mice than wild-type strains (Miyazaki, S. et al., J Med Microbiol 43:169-75, 1995), and that immunization directed against ETA increased survival in normal and thermally injured mice infected by *P. aeruginosa* (El-Zaim, H. S. et al., Infect Immun 66:5551-4, 1998). For DT, vaccination with a non-toxic mutant DT is widely used worldwide to prevent diphtheria infections.

The diphtheria toxin (DT) and the *Pseudomonas* exotoxin A (ETA) are two bacterial toxins having A and B subunits. These toxins are characterized by a B moiety that recognizes the cell surface receptor but that also plays a role in the translocation of the toxin into the cytosol, and an A moiety that contains the catalytic activity of the toxin. When released into the cytosol, the A subunit can inactivate the elongation factor-2 (EF-2) by inducing the ADP-ribosylation of a modified histidine residue called diphthamide, thus leading to cell death by blocking protein translation. The A subunit of DT and ETA present a high homology with the A subunit of other ADP-rybosyltransferases such as the cholera toxin of *Vibrio cholerae*, the heat-labile enterotoxin from *Escherichia coli*, the pertussis toxin from *Bordetella pertussis*, the C3-like exoenzyme from *Clostridium botulinum* and *Clostridium limosum*, as well as putative ADP-rybosyltransferases from *Neisseria gonorrhoeae*, *Staphylococcus aureus* and *Thermoanaerobacter teng*.

Diphthamide biosynthesis occurs on $His^{715}$ of EF-2 ($His^{699}$ in yeast) following the translation of EF-2, and consists of stepwise additions on its side chain (Liu, S. et al., Mol Cell Biol 24:9487-97, 2004). Five proteins have been identified as being involved in this process in yeast and mammals, namely Dph1 to Dph5 (Liu, S. et al., 2004). The biosynthesis of diphthamide occurs in three successive steps, involving Dph1, Dph2, Dph3 and Dph4 in the first step (3-amino-3-carboxypropyl transfer), and Dph5 in the second step (methyl transfer) (Liu, S. et al., 2004). So far, no protein has been identified as participating in the third step. This is at least partly due to the fact that the intermediate product diphtine resulting of the completion of the second step can also be ADP-ribosylated.

The biological role of diphthamide has not yet been determined, but it is found in all eukaryotic organisms and in archaebacteria except eubacteria, suggesting a relevant role in cell physiology (Liu, S. et al., Mol Cell Biol 26:3835-41, 2006). In the current state of the art, EF-2 is the only protein known with certainty to contain a diphthamide residue. But even if the role of diphthamide is unclear, some reports tentatively claim that it may play a role in EF-2 regulation, structure or stability (Kimata, Y., and Kohno, K., J Biol Chem 269:13497-501, 1994; Ortiz, P. A., and Kinzy, T. G., Nucleic Acids Res 33:5740-8, 2005).

Dph proteins are encoded by dph genes, which are highly evolutionary conserved among eukaryotes, thus suggesting that they have an important role in cell biology. Several yeasts and CHO cell lines lacking the expression of the different dph genes have been generated after exposure to mutagens (Chen, J. et al., Mol Cell Biol 5:3357-60, 1985; Kohno, K., T. et al., Somat Cell Mol Genet. 11:421-31, 1985), but none of these show distinctive phenotypes other than DT and ETA resistance, except for dph3.

The dph3 gene has been shown to be essential during mouse development (Liu, S. et al., 2006), since the loss of both dph3 alleles is lethal for the embryo. Furthermore, *Saccharomyces cerevisiae* cells lacking the capacity to express dph3 gene present growth defects and increased sensitivity to temperature and drugs (Liu, S. et al., 2004). Dph3 protein has been further shown to physically interact with the elongator complex in yeast, and its absence in yeast cell lines leads to the inhibition of the toxic action of zymocin (Fichtner, L. Et al., Mol Microbiol 49:1297-307, 2003). Dph3 seems to prevent the proteolysis of a protein that is part of the elongator complex, thus suggesting an important role of Dph3 in this complex's function/regulation. Dph1 and Dph2 proteins have also been shown to interact with the elongator complex by TAP-tagging. Therefore, those three proteins seem to play a certain role in other processes than just the biosynthesis of diphthamide.

More recently, it has been shown that the elongator complex and Dph3 are both required in yeast for the biosynthesis of modified nucleosides present at the wobble position in tRNA (Huang, B. et al., RNA 11:424-36, 2005). These modified nucleosides seem to be mostly involved in the decoding process of mRNA, in addition to acting as identity elements in amino-acyl-tRNA synthetase recognition.

The dph1 gene has also been cloned independently as ovca1 in ovarian cancer cells (Chen, C. M., and Behringer, R.

R., Genes Dev 18:320-32, 2004) where its expression is absent in about 80% of the tumors. In mice, dph1 acts as a tumor suppressor, as knockout mouse embryonic fibroblasts (MEFs) show proliferation defects related to a reduction of retinoblastoma 1 (Rb1) phosphorylation. It has also been shown by the same group that the loss of tumor protein 53 (p53) conferred the ability to rescue the proliferation defects of ovca1-knockout MEFs. Foremost, the ovca1 heterozygote mice develop cancer spontaneously. The dph1 gene is also essential to mouse development as the ovca1$^{-/-}$ mice die at birth or before (Chen, C. M., and Behringer, R. R., 2004).

In the 1940s and 1950s, a vaccine program based on diphtheria toxoid had nearly eliminated diphtheria in industrialized countries. However, recent outbreaks of diphtheria have been reported in various countries including Russia and the newly independent states of the former Soviet Union, and in socio-economically disadvantaged groups living in crowded conditions in Europe and in the US. The level of immunity against DT declines in late childhood and adolescence, and serological surveys showed that more than 50% of adults lack immunity to DT in some industrialized countries. Therefore, the lack of immunity against diphtheria in adults represents a potential threat that could lead to the development of epidemics in industrialized countries. Since those pathogens are still a major cause of many health problems, some resulting in death, and despite immunization programs and the use of antibiotics, new ways of treating/preventing infections caused by both *C. diphtheria* and *P. aeruginosa* are highly desirable.

Autologous stem cell transplantation (ASCT) can be used for patients with hematologic malignancies like Hodgkin and non-Hodgkin lymphomas, multiple myelomas and leukemias, as well as for other tumor types. High-dose chemotherapy, total body irradiation or salvage therapy are often used as frontline treatments of these malignancies, thus making ASCT needed for stem cell support. Unfortunately, minimal residual disease is often present in bone marrow or peripheral blood of cancer patients, and purging techniques have yet to be developed in order to eliminate those contaminating tumor cells. Such purging techniques can be performed ex vivo with chemotherapeutic drugs (such as cyclophosphamide-derived drugs), monoclonal antibodies and complement, and negative or positive selection (CD34+). In vivo purging is also an option with the use of Rituximab (an anti-CD20 monoclonal antibody) and chemotherapeutic agents for B cell malignancies. However, several side effects are associated with those ex vivo or in vivo purging approaches, such as delayed engraftment, loss of progenitor cells and high frequency of life-threatening infections. Furthermore, these techniques also appears to have an insufficient purging efficacy. US patent 2005/0287116 teaches the transfection of a mutant hamster EF-2 gene into cells, the mutant hamster EF-2 presenting a Arg$^{717}$ mutation changing the arginine for a glycine. This was shown to confer sufficient cell resistance to diphtheria toxin for the production of adenoviral vectors having the capability of carrying DT subunit DT-A.

It would also be highly desirable to have a resistance gene, that is not an antibiotic resistance gene, and that can be used as a genetic marker to select for genetically modified cells.

BRIEF SUMMARY OF THE INVENTION

According to an aspect of the present invention, there is provided an isolated dph2(C-) gene consisting of an isolated dph2 gene having a 3' end deletion of between 10 and 395 nucleotides, and in a further aspect of the present invention, the isolated dph2 gene is having the nucleotide sequence of SEQ ID NO:1 or SEQ ID NO:7. In yet a further aspect, the isolated dph2(C-) gene is having the nucleotide sequence of at least one of SEQ ID NO:3, SEQ ID NO:5, and SEQ ID NO:9. In yet a further aspect of the present invention, the isolated dph2(C-) gene is comprised in an expression vector, such as a viral vector.

According to another aspect of the present invention, there is provided an isolated dph2(C-) gene consisting of an isolated dph2 gene having a 3' end deletion of between 10 and 395 nucleotides. According to a further aspect, the 3' end deletion is of between 50 and 395 nucleotides. According to a further aspect, the 3' end deletion is of between 100 and 375 nucleotides. According to a further aspect, the 3' end deletion is of between 150 and 375 nucleotides. According to a further aspect, the 3' end deletion is of between 200 and 375 nucleotides. According to a further aspect, the 3' end deletion is of between 200 and 350 nucleotides. According to a further aspect, the 3' end deletion is of between 250 and 350 nucleotides. According to a further aspect, the 3' end deletion is of between 200 and 300 nucleotides. According to a further aspect, the 3' end deletion is of between 250 and 300 nucleotides. According to a further aspect, the 3' end deletion is of about 275 nucleotides. According to a further aspect, the 3' end deletion is of about 300 nucleotides. According to a further aspect, the 3' end deletion is of about 325 nucleotides.

According to another aspect of the present invention, there is provided a method and a use for inducing a resistance to a toxin capable of ADP-ribosylating diphthamide in a cell by introducing an expression vector comprising the dph2(C-) gene as described herein into the cell. In yet another aspect, the toxin is a diphtheria toxin and/or a *Pseudomonas* exotoxin A. In yet a further aspect, the toxin is selected from the cholera toxin of *Vibrio cholerae*, the heat-labile enterotoxin from *Escherichia coli*, the pertussis toxin from *Bordetella pertussis*, the C3-like exoenzyme from *Clostridium botulinum* or *Clostridium limosum*, and the ADP-rybosyltransferases from *Neisseria gonorrhoeae, Staphylococcus aureus* or *Thermoanaerobacter teng.*

According to another aspect of the present invention, there is provided a method and a use for protecting or treating a subject, animal or human, against an infection caused by a bacteria producing a toxin capable of ADP-ribosylating diphthamide in the cells of the subject by introducing the expression vector as described herein into the cells of the subject ex vivo and administrating cells containing the expression vector into said subject. In yet another aspect, the bacteria is *Corynebacterium diphtheria* and/or *Pseudomonas aeruginosa*. In yet a further aspect, the bacteria is selected from *Vibrio cholerae, Escherichia coli, Bordetella pertussis, Clostridium botulinum, Clostridium limosum, Neisseria gonorrhoeae, Staphylococcus aureus* and *Thermoanaerobacter teng.*

According to another aspect of the present invention, there is provided a method and a use for increasing the yield, by a viral producer cell, of a recombinant virus producing a toxin capable of ADP-ribosylating diphthamide by introducing the expression vector as described herein into the viral producer cell. In yet another aspect, the toxin is a diphtheria toxin and/or a *Pseudomonas* exotoxin A. In yet a further aspect, the toxin is selected from the cholera toxin of *Vibrio cholerae*, the heat-labile enterotoxin from *Escherichia coli*, the pertussis toxin from *Bordetella pertussis*, the C3-like exoenzyme from *Clostridium botulinum* or *Clostridium limosum*, and the ADP-rybosyltransferases from *Neisseria gonorrhoeae, Staphylococcus aureus* or *Thermoanaerobacter teng.*

According to another aspect of the present invention, there is provided a method and a use for selecting a cell resistant to a toxin capable of ADP-ribosylating diphthamide by introducing the expression vector as described herein into the cell, and then by contacting the cell with a toxin capable of ADP-ribosylating diphthamide. In yet another aspect, the toxin is a diphtheria toxin and/or a *Pseudomonas* exotoxin A. In yet a further aspect, the toxin is selected from the cholera toxin of *Vibrio cholerae*, the heat-labile enterotoxin from *Escherichia coli*, the pertussis toxin from *Bordetella pertussis*, the C3-like exoenzyme from *Clostridium botulinum* or *Clostridium limosum*, and the ADP-rybosyltransferases from *Neisseria gonorrhoeae*, *Staphylococcus aureus* or *Thermoanaerobacter teng*.

According to another aspect of the present invention, there is provided an isolated Dph2(C-) protein consisting of an isolated Dph2 protein having a C-terminal deletion of between 4 and 132 amino acids, and in a further aspect, the isolated Dph2 protein has the amino acid sequence of SEQ ID NO:2 or SEQ ID NO:8. In yet a further aspect, the isolated Dph2(C-) protein has the amino acid sequence of SEQ ID NO:4, SEQ ID NO:6, or SEQ ID NO:10.

According to another aspect of the present invention, there is provided an isolated Dph2(C-) protein consisting of an isolated Dph2 protein having a C-terminal deletion of between 17 and 132 amino acids. According to a further aspect, the C-terminal deletion is of between 34 and 125 amino acids. According to a further aspect, the C-terminal deletion is of between 50 and 125 amino acids. According to a further aspect, the C-terminal deletion is of between 67 and 125 amino acids. According to a further aspect, the C-terminal deletion is of between 67 and 117 amino acids. According to a further aspect, the C-terminal deletion is of between 84 and 117 amino acids. According to a further aspect, the C-terminal deletion is of between 67 and 100 amino acids. According to a further aspect, the C-terminal deletion is of between 84 and 100 amino acids. According to a further aspect, the C-terminal deletion is of between 90 and 100 amino acids. According to a further aspect, the C-terminal deletion is of about 91 amino acids. According to a further aspect, the C-terminal deletion is of about 95 amino acids. According to a further aspect, the C-terminal deletion is of about 100 amino acids.

According to another aspect of the present invention, there is provided a method and a use for inhibiting the formation of diphthamide in a cell by contacting the cell, in vivo or in vitro, with the isolated Dph2(C-) protein as described herein. According to a further aspect, there is provided a method and a use for inhibiting the formation of diphthamide in a cell by contacting the cell, in vivo or in vitro, with a mimic of the isolated Dph2(C-) protein as described herein.

According to another aspect of the present invention, there is provided a method and a use for decreasing or inhibiting the ADP-ribosylation of EF-2 in a cell by contacting the cell, in vivo or in vitro, with an isolated Dph2(C-) protein, or a mimic thereof.

According to a further aspect of the present invention, there is provided a composition comprising the isolated Dph2(C-) protein as described herein and an adjuvant. According to a further aspect, there is provided a composition comprising a mimic of the isolated Dph2(C-) protein as described herein and an adjuvant.

According to another aspect of the present invention, there is provided a method and a use for the prevention or treatment of an infection caused by *Corynebacterium diphtheria* and/or by *Pseudomonas aeruginosa* in a subject, animal or human, by administering to the subject a composition comprising the composition as described herein. In a further aspect, there is also provided a method and a use of the isolated Dph2(C-) protein as described herein for manufacturing a medicament for the prevention or treatment of an infection caused by *Corynebacterium diphtheria* and/or by *Pseudomonas aeruginosa* in a subject. In a further aspect, there is also provided a method and a use of a mimic of the isolated Dph2(C-) protein as described herein for manufacturing a medicament for the prevention or treatment of an infection caused by *Corynebacterium diphtheria* and/or by *Pseudomonas aeruginosa* in a subject. In yet a further aspect, the infection is caused by a bacteria selected from *Vibrio cholerae*, *Escherichia coli*, *Bordetella pertussis*, *Clostridium botulinum*, *Clostridium limosum*, *Neisseria gonorrhoeae*, *Staphylococcus aureus* and *Thermoanaerobacter teng*.

According to another aspect of the present invention, there is provided a method and a use for alleviating a side effect in a subject, animal or human, of an immunotoxin treatment or a ligand-toxin treatment comprising a toxin capable of ADP-ribosylating diphthamide by administering to the subject the composition as described herein. In a further aspect, there is also provided a method and a use of the isolated Dph2(C-) protein as described herein for manufacturing a medicament for alleviating a side effect in a subject, animal or human, of an immunotoxin treatment or a ligand-toxin treatment comprising a toxin capable of ADP-ribosylating diphthamide. In a further aspect, there is also provided a method and a use of a mimic of the isolated Dph2(C-) protein as described herein for manufacturing a medicament for alleviating a side effect in a subject, animal or human, of an immunotoxin treatment or a ligand-toxin treatment comprising a toxin capable of ADP-ribosylating diphthamide.

In the following description of the present product, terms and expressions are used in the following manner;

The expression "3' end deletion" as used herein is intended to represent the deletion of a portion of a nucleic acid sequence from its 3' end toward the 5' portion of the nucleic acid sequence. For example, a 3' end deletion of between 10 and 395 nucleotides represents the deletion of between 10 and 395 nucleotides starting from the nucleotide at the 3' end of the nucleic acid sequence and consecutively toward the 5' end, from a minimum deletion of 10 consecutive nucleotides to a maximum deletion of 395 consecutive nucleotides.

The expressions "C-terminal deletion" and "(C-)" as used herein is intended to represent the deletion of a portion of an amino acid sequence from its C-terminal portion toward the N-terminal portion of the amino acid sequence. For example, a C-terminal deletion of between 4 and 132 amino acids represents the deletion of between 4 and 132 amino acids starting from the amino acid at the C-terminal portion of the amino acid sequence and consecutively toward the N-terminal portion, from a minimum deletion of 4 consecutive amino acids to a maximum deletion of 132 consecutive amino acids. The expression "(C-)" as used herein when applied to a gene is intended to reflect a 3' end deletion of the gene equivalent to that of a C-terminal deletion in the protein encoded by the gene, as described herein.

The expression "expression vector" as intended herein is intended to include any natural or artificial genetic material suitable for the incorporation of a nucleic acid sequence within it, and equipped with the necessary genetic elements to allow the expression of a peptide, polypeptide or protein encoded by the nucleic acid sequence incorporated. Examples of such expression vectors include viral vector and plasmid vector. The expressions "introducing an expression vector into a cell" and the likes, as used herein, are intended to encompass all the means, methods and techniques in vivo and in vitro, by which an expression vector can be introduced into a cell, such as, without being limited to, transfection, transduction, infection, transformation and electroporation. The expected result of the introduction into a cell of an expression vector containing a nucleic acid sequence will be the incorporation of the nucleic acid sequence into the genetic material of the cell in a way that will allow the cell to express the peptide, polypeptide or protein encoded by the nucleic acid sequence.

The expressions "toxin resistance" and "resistance to a toxin" as used herein are intended to reflect the absence of response of a cell or an organism when contacted with a toxin to which the cell or organism would normally respond. Examples of responses to a toxin include, but are not limited to, cell death, lack of cell division, changes in state or activity such as a change in movement, secretion, enzyme production, gene expression, viability, etc.

The expression "protecting or treating a subject against an infection" and the likes as used herein are intended to represent the addition in the subject of a mean to resist, totally or partially, to an infection as defined in the text, or a mean to reduce, totally or partially, the presence of an infection as defined in the text, or to reduce the effects or symptoms related to the infection as defined in the text. The protection can occur in a subject in which the infection has never occurred, is expected to occur, or has started to occur in a way that the protection will prevent the infection from spreading in the subject or from having an increased effect or related symptoms, when compared to an infection in a subject that would not be treated.

The expression "increasing the yield of a recombinant virus" as used herein is intended to represent an increase in the number of recombinant viruses produced in a given length of time as compared with the number of recombinant viruses usually expected and normally produced in the same length of time. The expression "viral producer cell" as used herein is intended to mean any cell that can be used for the production of a virus or a recombinant virus (e.g. a genetically engineered virus) of interest in a directed and expected manner.

The term "mimic" as used herein is intended to encompass any molecule having a structure or a property for a specific goal similar to the one of a molecule of interest. In the present application, a "Dph2(C-) mimic" is intended to represent a natural or artificial molecule presenting the same properties as Dph2(C-) for a specific application, such as the inhibition of the formation of diphthamide, the decrease or inhibition of ADP-ribosylation of EF-2, the prevention or treatment of an infection caused by C. diphtheria or P. aeruginosa, or the alleviation of a side effect of an immunotoxin treatment or a ligand-toxin treatment in a subject. The Dph2(C-) mimic therefore present an activity similar to that of Dph2(C-) on diphthamide formation, that is a capacity to form a complex with Dph1 while being incapable to induce diphthamide formation from a histidine residue.

The term "adjuvant" as used herein is tended to encompass any adjuvant that is suitable for the administration or delivery of a Dph2(C-) protein or mimic in a cell or organism, to any delivery route that might be suitable for the Dph2(C-) protein or mimic to exert the intended effect, such as, but not limited to, intravenous delivery, intramuscular delivery and oral delivery. Examples of such adjuvants can include excipients and pharmaceutical adjuvants having no or little biological effects while increasing or modulating the efficacy or potency of the administered Dph2(C-) protein or mimic.

The expression "alleviating a side effect" as used herein in relation with an immunotoxin treatment or a ligand-toxin treatment is intended to represent the alleviation of a side effect normally occurring as a result of the immunotoxin treatment or the ligand-toxin treatment.

BRIEF DESCRIPTION OF THE DRAWINGS

Having thus generally described the nature of the invention, reference will now be made to the accompanying drawings, showing by way of illustration, a preferred aspect thereof, and in which:

FIG. 1 illustrates the structure of the hamster Dph2 protein (SEQ ID NO:2) and the Dph2(C-) having a 91 amino acid deletion in C-terminal (SEQ ID NO:6);

FIG. 2 illustrates the protective effect of Dph2(C-) protein against DT toxicity in CHO cells;

FIG. 3 illustrates the protective effect of Dph2(C-) protein against DT toxicity in 293T cells;

FIG. 4 illustrates the protective effect of Dph2(C-) protein against ETA toxicity in CHO cells;

FIG. 5 illustrates the proposed ADP-ribosylation process of the diphthamide residue in EF-2 as modulated by DT and ETA;

FIG. 6 illustrates the proposed conversion of the $His^{175}$ residue of EF-2 into diphthamide, and the involvement of Dph1, Dph2, Dph3 and Dph4 proteins in this conversion;

FIG. 7 illustrates the effect of Dph2 C-terminal deletion mutant ((C)iPuro), N-terminal deletion mutant ((N)iPuro) and leucine zipper deletion mutant ((Z)iPuro) on the ADP-ribosylation of EF-2 in CHO cells. RPE.33d cells were used as a negative control, while RPE.33d cells transfected with native Dph2 (RPE Dph2iPuro) were used as a positive control. (A) Radioassay with radiolabeled $NAD^{14}$ and fully nicked DT addition to the different cell extracts. The extracts were ran on a SDS-PAGE gel and autoradiography was performed on the gel. (B) Detection of EF-2 in cells extract with an anti-EF-2 antibody. (C) cpm counts reflective of ADP-rybosylation of EF-2;

FIG. 8 illustrates the effect of C-terminal Dph2 deletion mutant. (A) Dph2 and Dph2 deletion mutants. (B) Dph2(C-) confers DT resistance in TE671 cells. TE671 cells untransfected and transfected with dph2(C-), dph2(N-) or dph2(Z-) were selected with DT for 7 days. Cells were then fixed with MeOH and stained with methylene blue. (C) The viability of CHO (♦), RPE.33d (Δ), RPE.33d transfected with dph2 (O) and CHO transfected with dph2(C-) (■) cells was measured 3 days after culturing cells with increasing DT concentrations. The cell viability was measured using the MTT proliferation assay. Data are expressed as a proliferation percentage relative to the proliferation of cells in the absence of drug and are the average of six values±SD; and FIG. 9 illustrates that Dph2(C-) binds to Dph1 and competes with Dph2. Western blot analysis performed with an anti-TAP antibody from cellular extracts immunoprecipitated with an anti-myc antibody. Lane 1, untransfected 293T cells were used as control; lane 2, pcDNA-Dph1-myc (1 μg) and pNC-Dph2(C-)-TAP (1 μg) plasmids were transfected; lane 3-5, pcDNA-Dph1-myc (1 μg) and pNC-Dph2-TAP (1 μg) plasmids were transfected with 0, 1 and 10 μg of pMD-Dph2 (C-) plasmid.

DETAILED DESCRIPTION OF THE PREFERRED ASPECT

The present application describes deletion mutants of the C-terminal part of Dph2 (Dph2(C-)), for example, a hamster deletion mutant Dph2 having 91 amino acids (aa) deleted from its C-terminal portion (FIG. 1). The dph2(C-) gene was constructed from the hamster dph2 gene encoding 489 aa (SEQ ID NO:1 and SEQ ID NO:2). PCR amplification of the gene was performed from cDNAs obtained from a CHO-K1 cell line. The deletion mutant dph2(C-) encodes for the first 398 amino acids of Dph2 with an asparagine residue as the last aa (SEQ ID NO:5 and SEQ ID NO:6). This extra amino acid is caused by the PCR strategy used to create the deletion mutant. Without the application of this PCR strategy, the dph2(C-) gene goes in-frame with the cloning vector, encoding a Dph2(C-) protein having six amino acids originating from the vector (SEQ ID NO:3 and SEQ ID NO:4).

Human deletion mutant dph2(C-) genes and proteins are also described herein, with a C-terminal deletion of the human dph2 gene (SEQ ID NO:7) of 300 nucleotides (SEQ ID NO:9). This deletion mutant encodes a protein with a decreased length when compared to the human Dph2 protein (SEQ ID NO:8), having a length of 398 aa (SEQ ID NO:10).

Figure 2:
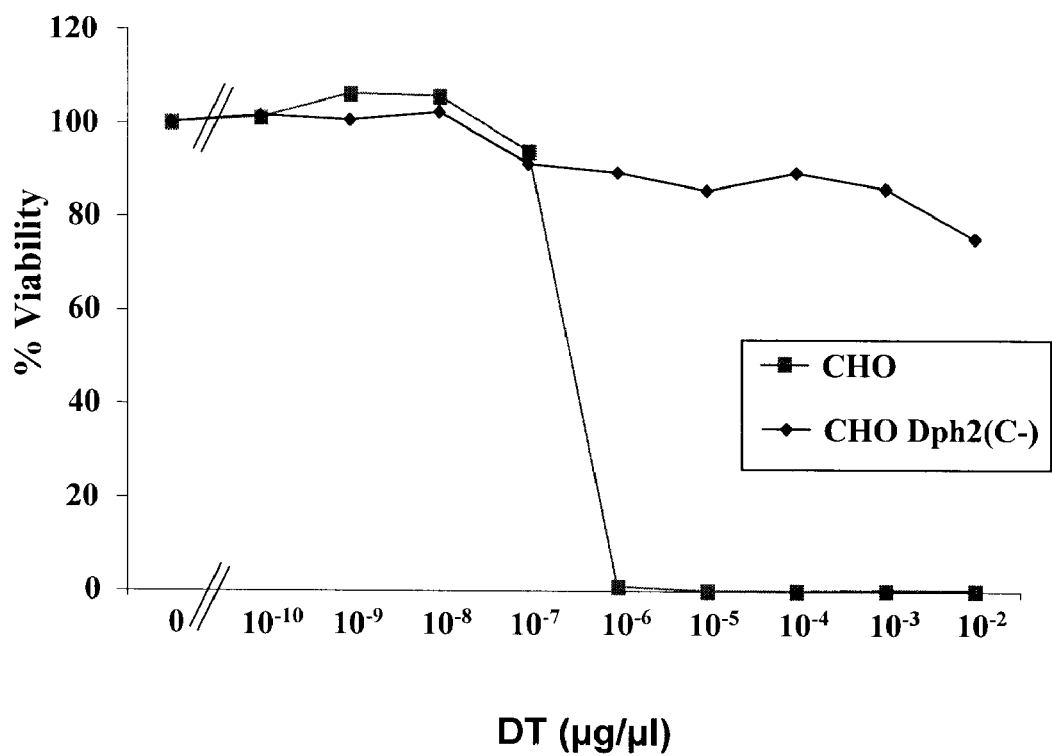
Figure 3:
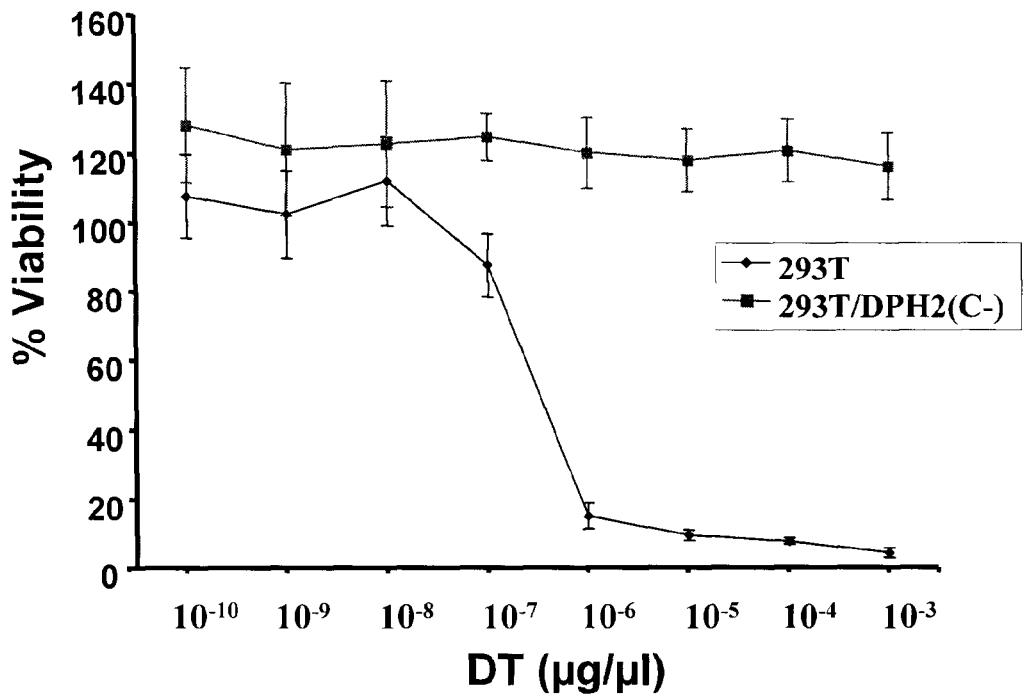
Figure 8:
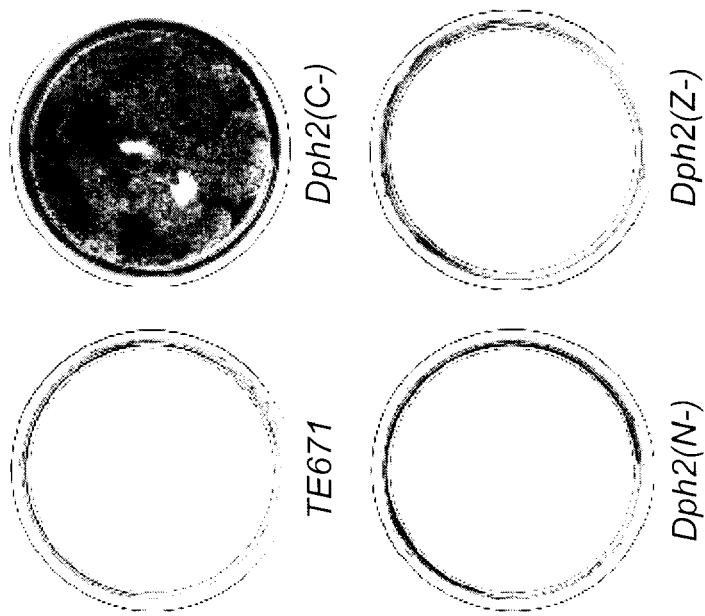
Figure 8:
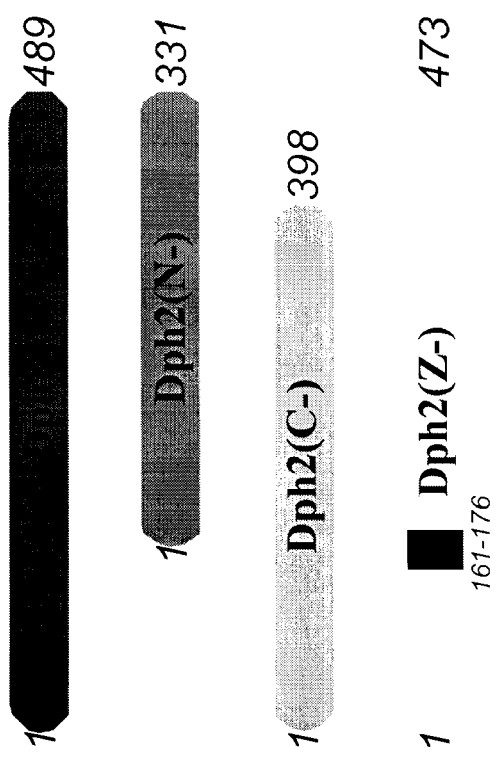
Figure 8:
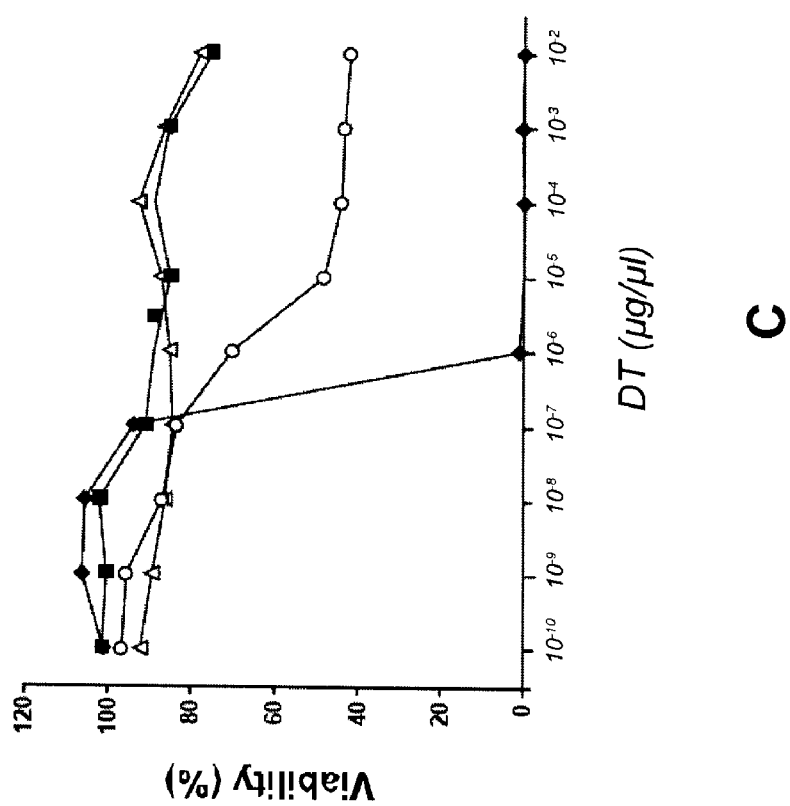

Generally, a dph2(C-) gene was cloned in an eukaryotic expression vector and transfected into CHO-K1 cells (hamster cells) or 293T cells (human embryonic kidney cells). Transfected cells were selected with DT at $5\times10^{-5}$ mg/ml, which represents a dose that kills untransfected cells in less than 3 days. In a dose-response experiment involving culturing cells for three days and evaluating their proliferation with a 3-(4,5-dimethylthiazol-2-yl)-2,5-diphenyltetrazolium bromide (MTT) assay, cells expressing the dph2(C-) gene were shown to be completely protected from DT toxicity (FIG. 2, FIG. 3 and FIG. 8C). A similar protection to ETA was also seen with cells expressing the dph2(C-) gene (FIG. 4).

DT and ETA act by ADP-ribosylating the diphthamide residue present on EF-2 (FIG. 5). The Dph2(C-) protein acts by inhibiting, in a dominant manner, the conversion of the histidine at position 715 of EF-2 into diphthamide.

In the first step of diphthamide formation, $His^{715}$ of EF-2 is converted into an "intermediate" molecule by receiving a 3-amino-3-carboxypropyl group. It has been demonstrated in complementation experiments in yeasts that four proteins named Dph1, Dph2, Dph3 and Dph4 are involved in this modification of $His^{715}$ into this "intermediate" (FIG. 6). Dph1 and Dph2 have a strongly related sequence (16% aa identity in yeast and 19% aa identity in mice), and it has been shown by co-immunoprecipitation experiment that these two proteins interact with one another.

Without wishing to be bound by theory, by engineering a transdominant mutant of dph1 or dph2, it is speculated that it will be possible to block the formation of the "intermediate" molecule in the biosynthesis of diphthamide. It is thought that Dph2(C-) protein competes with Dph2 for binding to Dph1, thus leading to the absence of formation of the "intermediate" molecule. EF-2 from CHO cells expressing Dph2(C-) is not susceptible to the ADP-ribosylation by DT. Similar results were obtained for EF-2 in CHO cells that are defective for Dph2 expression (RPE33.d) (FIG. 7).

The present application provides the induction of DT resistance in viral producer cells by transfecting those cells with a dph2(C-) gene, therefore allowing the production of recombinant virus that can carry DT-A (the catalytic subunit of DT), ETA or less toxic mutants thereof such as $DT\text{-}A^{CRM197}$, $DT\text{-}A^{H21G}$ and $DT\text{-}A^{H21F}$.

The production of viral vectors having the capacity to deliver, for example, the A subunit of DT (DT-A) has been difficult to achieve due to the severe toxicity of DT-A to cells occurring during viral production. Such a vector containing DT-A would be extremely useful for eliminating cells, for example in the treatment of solid tumors as well as for stem cells purging. In one aspect of the present application, viral producer cells have been transfected or co-transfected with a dph2(C-) gene, rendering the cells resistant to DT and thus capable of producing vectors containing DT-A more efficiently. According to another aspect of the present application, such a viral vector can be injected directly into a tumor, or can be administered in a diffuse manner, i.e. by intravenous administration or intraperitoneal administration for example, since it possess the ability to target tumor cells.

Another aspect of the present application is to develop an artificial molecule, or a drug, having the capacity to mimic the activity of Dph2(C-) protein. Another aspect of the present application is to provide tools, such as gene and protein sequences, to develop artificial molecules and drugs having the capacity to mimic the activity of Dph2(C-) protein. Such artificial molecule or drug would be useful for the treatment of diphtheria and *P. aeruginosa* infections.

In developing countries, vaccination of children against diphtheria has so far proven to be efficient. Nevertheless, as a child becomes older, the level of antibodies directed against DT decreases over time, and it remains unclear to which extent older adults are protected. Religious beliefs can also be a reason why one would not be vaccinated at all in the first place. Again, such a Dph2(C-) mimic having the potential to disrupt the effect of DT would be of particular use, with administration routes not exclusively restricted to vaccination. In such a case, administration of Dph2(C-) mimic could represent a therapeutic or preventive treatment, for example of major burn victims.

Moreover, with bioterrorism being a major threat to developing countries, and the possibility that biological weapons containing DT or ETA could be engineered and used at large scale, drugs that could rapidly counteract the activity of these toxins and that would be readily available, such as a Dph2(C-) mimic, would then prove to be particularly useful.

In addition, a Dph2(C-) mimic could also be used in alleviating the side effects caused by immunotoxins or other specific ligands coupled to toxins, such as DT, that are used in the treatment of particular pathologies, such as cancer. Therapeutic immunotoxins, coupling a toxin capable of disrupting a cell with an immunologic molecule allowing the specific or semi-specific targeting of the particular cell type to be disrupted, have already been developed, particularly for the treatment of glioblastoma (DTIL13, DTIL4, etc) or T cell malignancies (DTIL2, denileukin diftitox). For example, when an immunotoxin containing DT is delivered directly into the brain, it would be possible to decrease the side effects caused by this treatment outside of the brain by injecting a Dph2(C-) mimic that would be efficient against DT and that would not pass the blood brain barrier.

Another aspect of the present application is the use of dph2(C-) gene in the selection of transfected cells, either during laboratory experiments or for gene therapy applications. Vectors currently used for gene therapy, such as retroviral and lentiviral vectors, integrate their genome into the host DNA, and are therefore responsible for potential insertional mutagenesis. For safety reasons it is then preferable to introduce only one copy of the vector per cell. The use of a low multiplicity of infection that would result in less than 20% of cells being infected could be coupled with DT selection for the enrichment of transduced cells.

One of the advantage of dph2(C-) selection over current selection methods is the high speed at which the selection can be achieve with DT. Cells can be selected after as little as 1 to 2 days, while most of the other selection procedures need 7 to 10 days to perform. This is an overwhelming advantage for ex vivo stem cell gene transfer. For example, it is known that haematopoietic stem cells undergo differentiation if they are kept for a long period of time in vitro. A shortened culture time therefore reduces the chances of stem cells to undergo spontaneous and unwanted differentiation. Therefore, stem cells containing a dph2(C-) gene will not change phenotype during culture time and keep their grafting properties. Also, shortened in vitro culture time decreases the costs of the cell culture as well as the risk for contaminations by pathogens. The high level of DT resistance mediated by dph2(C-) (a thousand-fold resistance level, i.e. three orders of magnitude, is seen with 293T cells and CHO-K1 cells) precludes the absence of toxicity of DT on the cells containing dph2(C-) gene.

In current selection methods, several resistance genes are commonly used for selection of transfected cells, most of them being derived from bacteria (Puro$^r$, Neo$^r$, Zeo$^r$, Hygro$^r$). The downside of this is that when the transgene have to be re-administered to a patient for gene therapy applications, there is a chance that the transgene product can be recognized by the immune system of the patient because of the bacterial sections coming from the resistance gene. This can lead to the elimination of the genetically modified cells. By opposition, Dph2(C-) is a human protein, and its expression does usually not lead to an immune response in humans. This is a tremendous advantage ensuring that transgene products will not lead to the elimination of the transgenic cells in vivo.

Other human genes conferring a resistance to chemotherapeutic agents have been previously described, such as MDR-1, MRP, DHFR, and MGMT, but their conferred resistance is limited. As a consequence, low doses of chemotherapeutic agents can be used, leading to longer exposure time, as for example when selecting haematopoietic stem cells. Also, if the cells in which such resistance genes have been introduced inadvertently become malignant, these cells would be resistant to chemotherapeutic agents. For example, the human dph2(C-) gene is 1197 nucleotides long and can therefore easily be cloned in a retroviral vector or a lentiviral vector, leaving sufficient space for the addition of a therapeutic gene in the vector. The packaging capacity of those vectors is limited to approximately 7 to 8 kb. The use of long resistance genes, such as MDR-1 gene, which is 4.1 kb, greatly limits the use of long therapeutic genes in retroviral and lentiviral vectors. By allowing the use of longer therapeutic genes, or even multiple therapeutic genes, dph2(C-) present an undeniable advantage over currently existing systems.

According to another aspect of the present invention, there is provided an application of dph2(C-) gene in gene therapy. For example, for ex vivo gene therapy applications, it is often necessary to make a selection of the cells before re-injecting them into the patient. Such a selection can be performed by the methods described herein and above.

An example of a situation in which a selection of the cells should be performed before re-injecting them into a patient is allogenic bone marrow transplantations. Those types of transplantation are often linked to graft versus host disease (GVHD), which is a fatal complication that occurs in about 10 to 20% of the patients undergoing allogenic bone marrow transplantations. It is well known that the T-lymphocytes present in the bone marrow are important for the success of the graft, particularly for controlling potential viral infections (such as with Epstein Barr virus or cytomegalovirus) and for eliminating tumor cells in cancer patients. Unfortunately, these T-cells can also attack healthy tissues of the recipient, thus causing GVHD. To control GVHD, it has been proposed to introduce the herpes simplex virus thymidine kinase (TK) gene into the bone marrow T-cells. After separation and transduction of the T-cells, they would be mixed back with the haematopoietic stem cells before grafting. In the case where GVHD would occur as a result of the transplantation, the T-cells could be eliminated with ganciclovir that would kill cells specifically containing TK. The success of this strategy depends on the proportion of T-cells containing TK, with a higher number of TK-containing T-cells being reflective of higher chances of controlling GVHD. By introducing the dph2(C-) gene into the TK vector and subsequent selection of T-cells with DT, it would allow for the selection and re-injection of a higher number of TK-containing T cells, thus improving the chances of successfully controlling GVHD.

Another example of cell selection using Dph2(C-) is applicable to the treatment of X-linked chronic granulomatous disease (X-CGD), which is caused by mutations in any of the 4 genes encoding the subunits of the nicotinamine dinucleotide phosphate oxidase complex that impair the antimicrobial activity of phagocytes. Gene transfer of those corrected 4 genes into haematopoietic stem cells has been proposed as a possible therapeutic option, but it is admitted that a high number of genes-corrected-cells would be necessary to obtain a correction of the global phenotype. Introduction of the dph2(C-) gene into haematopoietic cells having those 4 corrected genes, such as by inserting the dph2(C-) gene into the therapeutic gene, when followed with subsequent selection with DT, would allow for an enrichment of haematopoietic gene-corrected-cells, thus increasing the number of adequate cells and therefore increasing the effect on the global phenotype.

The present invention will be more readily understood by referring to the following examples which are given to illustrate the invention rather than to limit its scope.

EXAMPLES

Example 1

DNA Constructions

The hamster dph2 gene was amplified by RT-PCR from CHO-K1 cells using the mouse 5' primer: dph2E-5' (5'-ATCGAATTCATGGAGTCTACGTTCAGCAG-3' (SEQ ID NO:11)) containing an EcoRI site (underlined) and a 3' degenerated primer designed according to the mouse and human dph2 sequence: 5'-TCAGCNGCTNCCCTCATC-3' (SEQ ID NO:12). The pBS-Dph2 plasmid was then obtained by cloning the PCR product in pBluescript SK+ (Stratagene, La Jolla, Calif.) opened in EcoRI/EcoRV. Three deletion mutants of dph2 were constructed by PCR using pBS-Dph2 as template, and they were cloned in the following eukaryotic vectors: pMD2iPuro$^r$, pcDNA3-TAP and pNC. pcDNA3-TAP and pNC are well known in the art, while pMD2iPuro$^r$ contains the cytomegalovirus immediate early promoter followed by a human β-globin intron, a polylinker and a puromycin-resistant gene driven by an internal ribosomal entry site (IRES).

The hamster dph2 gene was also amplified without the stop codon of the previously described dph2 gene (so it can be put in frame with the TAP tag) by performing a PCR with the following primers: dph2K-5' (5'-CGGGGTACCATGGAGTCTACGTTCAG-3' (SEQ ID NO: 13)) containing a KpnI site (underlined) and 3' primer: dph2B-3' (5'-CGCGGATCCGCCGCTGCCCTCATCCT-3' (SEQ ID NO:14)) containing a BamHI site (underlined). The KpnI/BamHI digested PCR product was then cloned into pcDNA3-TAP opened in KpnI/BamHI to create the pcDNA-Dph2-TAP plasmid.

The C-terminal deletion mutant (Dph2(C-)) was constructed from dph2(C-) by PCR with the 5' primer: dph2K-5' and the 3' primer: 5'-GAATTCGGGAGTGGAACATA-3'

(SEQ ID NO:15). The pcDNA-Dph2(C-)-TAP plasmid was obtained by cloning the KpnI digested PCR fragment in pcDNA3-TAP opened in BamHI blunted by klenow and KpnI.

pNC-Dph2-TAP and pNC-Dph2(C-)-TAP were generated by cloning Dph2-TAP and Dph2(C-)-TAP linked to a BamHI adaptor into pNC opened in BamHI.

The pMD2-Dph2iPuro$^r$ was constructed by cloning Dph2 from pBS-Dph2 digested by EcoRI/XhoI into pMD2iPuro$^r$ opened in EcoRI/XhoI.

The pMD2-Dph2(C-)iPuro$^r$ plasmid was constructed by inserting a dph2(C-) PCR product with the 5' primer: dph2E-5' and the 3' primer: 5'-TTAATTCGGGAGTGGAACAT-3' (SEQ ID NO:16) digested by EcoRI and inserted into pMD2iPuro$^r$ opened by EcoRI/EcoRV.

For the construction of the N-terminal deletion mutant (N-), the PCR amplification was performed using the 5' primer: 5'-CGCGGTACCATGGAGCCAGCTTGTGC-3' (SEQ ID NO:17) containing a KpnI site (underlined) and the 3' primer: dph2B-3'. The PCR product was digested by KpnI and BamHI and ligated into the pcDNA3-TAP plasmid to give the pcDNA-Dph2(N-)-TAP plasmid.

The leucine zipper deletion mutant (Z-) was designed using the "PROSITE" program that identified a putative leucine zipper motif between residues 160-181. Two different PCR fragments have been ligated together in pcDNA3-TAP. The first segment was amplified with the 5' primer: dph2K-5' and the 3' primer: 5'-GGCATGGGCACAAGCTG-3' (SEQ ID NO:18), while the second fragment was amplified with the 5' primer: 5'-ATCTCCAGCCCAGCTCTT-3' (SEQ ID NO:19) and the 3' primer: dph2B-3'. The pcDNA-Dph2(Z-)TAP plasmid was constructed by cloning the first amplification product digested by KpnI and the second one digested by BamHI in pcDNA3-TAP.

The pMD2-Dph2(N-)iPuro$^r$ and pMD2-Dph2(Z-)iPuro$^r$ plasmids were constructed similarly. Briefly, the KpnI/BamHI fragment from either pcDNA-Dph2(N-)-TAP or pcDNA-Dph2(Z-)-TAP was blunted with klenow and ligated into pMD2iPuro$^r$ vector digested by EcoRV and XbaI blunted by klenow. A stop codon was created at the C-terminal end due to the cloning procedure.

The mouse dph1 gene was amplified by RT-PCR using cDNAs prepared from mouse PG13 cells with the following primers: 5' primer: 5'-ATGGCGGCGCTGGTA-3' (SEQ ID NO:20) and 3' primer: 5'-CGC GGATCCGGGAGCCGGCGAAGTA-3' (SEQ ID NO:21) containing a BamHI site (underlined). The PCR product was then digested by BamHI and ligated into pcDNA3.1 (-)/myc-His A (Invitrogen, Carlsbad, Calif.) to create the pcDNA-Dph1-myc vector.

Example 2

Tissue Culture and Transfections

CHO-K1 cells (ATCC CCL-61) were cultured in RPMI (Invitrogen, Carlsbad, Calif., USA), while 293T cells, TE671 cells and REP.33d cells were cultured in Dubelcco's modified Eagle's medium (DMEM) (Sigma, Oakville, ON, Canada), supplemented with 10% fetal calf serum (Bio Media Canada, Drummondville, QC, Canada) and antibiotics.

Transfection of 293T, TE671 cells and CHO-K1 cells were performed by the calcium phosphate method, whereas the RPE.33d cells were transfected using polyethylenimine, linear (PEI) (Polysciences Inc., Warrington, Pa., USA), PEI transfections were performed by mixing 2 µg of PEI per µg of DNA in 500 µl of serum-free DMEM for 15 min. The mixture was added to subconfluent cells in a 60-mm culture dish containing 5 ml of DMEM with 10% fetal calf serum. The transfection was performed overnight and the culture medium was changed the following day. Stable cell lines of CHO-K1 and RPE.33d were selected with 500 µg/ml and 600 µg/ml of G418 (70% active) (Invitrogen) for 2 weeks. Puromycin doses used for selection were respectively of 10 µg/ml and 5 µg/ml for 2 weeks. DT (Cedarlane Laboratories limited, Hornby, ON, Canada) doses used for selection of some CHO stable cell lines were of $5 \times 10^{-5}$ mg/ml.

Subconfluent TE671 cells plated in 60-mm plates were transfected with 2 µg of pMD2-Dph2(C-)iPuro$^r$, pMD2-Dph2(N-)iPuro$^r$ or pMD2-Dph2(Z-)iPuro$^r$ by the calcium phosphate procedure. The following day, cells were selected with DT at $5 \times 10^{-5}$ mg/ml, viable cells were fixed with MeOH and stained with methylene blue 7 days later.

Example 3

Cell Proliferation Assay

The cells were plated at a concentration of $3 \times 10^3$ cells/well in 96-well plates in six replicates for each toxin (DT or ETA) concentration. The next day, increasing concentrations of toxin were added to the wells and incubation was carried for 3 days. Cell proliferation was measured by a MTT assay (Sigma), which consists of adding 37.5 µl of MTT (1 mg/ml) to the 150 µl of medium contained in each well of a 96-well plate for 4 hours at 37° C. After gentle removal of the medium, 150 µl of dimethyl sulfoxide (DMSO) was added and the plates were gently shaken for 10 minutes to dissolve the formazan blue crystals. Absorbance was measured at 595 nm with a microplate reader (Tecan, Research Triangle Park, N.C., USA).

Example 4

ADP-Ribosylation Assay

Cells were grown in 60 mm plates, and were lysed in 400 µl of modified RIPA buffer (50 mM Tris-HCl, pH 7.4, 1% Nonidet P-40, 0.25% sodium deoxycholate, 150 mM NaCl, 1 mM EDTA and protease inhibitors (Sigma)) at 4° C. for 45 minutes. Cell extracts were then centrifuged at 13,000×g for 30 minutes at 4° C. before recovery of the supernatant and determination of the proteins concentration by the Bradford protein assay (Biorad, Hercules, Calif., USA). Nicking of DT was performed by mixing 27 µl DT (1 mg/ml) with 3 µl trypsin (10 mg/ml) for 15 minutes. The reaction was stopped by adding 1 µl of protein inhibitors (Sigma, P8340).

For the ADP-ribosylation assay, 100 µg of protein extract were mixed with 500 ng of nicked DT, 2 µl [$C^{14}$]NAD (GE Healthcare, 288 mCi/mmol), 20 mM Tris-HCl, pH 7.5, 50 mM dithiothreitol (DTT), 1 mM EDTA at 30° C. for 30 minutes in a final volume of 120 µl. From the 120 µl of the reaction, 50 µl were mixed with 17 µl of 4× sample buffer (200 mM Tris-HCl, 8% SDS, 0.4% bromophenol blue, 40% glycerol, 400 mM DTT) and analyzed by SDS-PAGE on a 10% acrylamide gel followed by autoradiography. The remaining 70 µl of the reaction were precipitated with 10% TCA (trichloroacetic acid), spotted on a glass microfibre filter (GF/C) and the radioactivity associated with EF-2 was determined with a scintillation counter.

Example 5

Immunoprecipitation 293T cells plated in 60-mm plates were transfected with 1 µg of the pcDNA-Dph1-myc plasmid with 1 µg of pNC- Dph2-TAP, and with 0, 1 or 10 μg of pMD2-Dph2(C-) plasmids. One μg of the pcDNA-Dph1-myc plasmid with 1 μg of pNC-Dph2(C-)-TAP were also transfected to assess the binding of Dph2(C-) with Dph1. Two days post-transfection, the cells were lysed in 500 μl of E1A buffer (20 mM HEPES pH7.9, 250 mM NaCl, 0.1% IGEPAL, 10% glycerol, 1 mM β-Mercaptoethanol and protease inhibitors) at 4° C. for 30 minutes. The lysis product was then incubated with 1 μg of the anti-myc antibody (clone 9E10) (Sigma) at 4° C. for 4 hours. Following this incubation, the extracts were treated with protein A-Sepharose (GE Healthcare Bio-Sciences) at 4° C. for 1 hour. The beads were then washed three times with E1A buffer and resuspended in 40 μl loading buffer (50 mM Tris-Cl pH6.8, 2% SDS, 0.1% bromophenol blue, 10% glycerol, 100 mM DTT).

Example 6

Western Blot Analysis

Thirty μg of total protein extract were mixed with loading buffer (as described above) and ran on a 10% SDS-polyacrylamide gel and separated by electrophoresis. Anti-TAP antibody (Open Biosystems, Huntsville, Ala.) was able to detect Dph2(C-)-TAP more efficiently than Dph2-TAP, so the Dph2(C-)-TAP sample was diluted before loading on gel. The proteins were transferred onto nitrocellulose membranes (GE Healthcare Bio-Sciences) followed by Western blotting using a goat antibody directed against a linear peptide of the carboxyl terminal of EF-2 (catalog no. Sc-13004; Santa Cruz Biotechnology, Inc., Santa Cruz, Calif., USA). The reactive bands were detected using the Western Lightning Chemiluminescence Reagent Plus kit (Perkin Elmer Life Sciences, Boston, Mass.).

Example 7

Deletion of 91 Residues in the C-Terminal Part of the Dph2 Gene Confers Resistance to Diphtheria Toxin in a Dominant Manner Not much is known about the Dph1-Dph2 protein structures, and the lack of information about the Dph1-Dph2 interactions led us to producing semi-random deletions in the dph2 gene. Three different deletions were produced. One at the C-terminal of Dph2 (Dph2(C-), 91 amino acids deleted), one at the N-terminal of Dph2 (Dph2(N-), 158 amino acids deleted), and one of residues 161-176 of Dph2 corresponding to the leucine zipper (Dph2(Z-), 16 amino acids deleted) (FIG. 8A). The nucleotide sequences encoding for each of the different Dph2 deletion mutants were cloned in a vector (pMD2.KGiPuro) that allowed the creation of stable cell lines expressing the Dph2 deletion mutants following puromycin selection. The three vectors containing each a dph2 deletion mutant were first transfected in CHO-K1 cells, and those cells were then treated with $5\times10^{-5}$ μg/ml DT for 10 days in order to determine whether any of the Dph2 deletion mutants could render CHO cells resistant to DT by blocking Dph1-Dph2 complex functionality. Cells transfected with the leucine zipper and N-terminal deletion mutants did not show any DT resistance, whereas cells transfected with the C-terminal deletion mutant were resistant to DT (FIG. 2). The same results were also obtained with human 293T cells (FIG. 3), HT1080 cells (data not shown), and TE671 cells (FIG. 8B). Without wishing to be bound by theory, this suggests that C-terminal deletions in Dph2 disrupt the Dph1-Dph2 complex functionality.

In order to investigate to what extent the Dph2(C-) confer resistance to DT, stable cell lines resistant to puromycin were produced from CHO-K1 cells transformed with the three different dph2 deletion mutants, while a RPE.33d cell line was stably transfected with a native dph2 gene cloned in the same pMD2.KGiPuro vector. RPE.33d cells have been reported to be resistant to DT due to the fact that they do not express the dph2 gene. A MTT proliferation assay was performed, and the cells transfected with either the Dph2(N-) or the Dph2(Z-) deletion mutants did not showed an increased resistance to DT when compared to CHO cells, whereas cells transfected with the Dph2(C-) deletion mutant were shown to be as resistant to DT as RPE.33d cells. The dominant DT resistance conferred by the Dph2(C-) deletion mutant is very strong since a concentration of $1\times10^{-2}$ μg/ml DT did not kill the transfected cells (FIG. 8C). This concentration is superior by four logs to the concentration effective for killing wild-type CHO cells. Each Dph2 deletion mutants were also tested for their diphthamide biosynthesis capacity in the RPE.33d cell line. None of the mutants were able to restore the formation of diphthamide in RPE.33d cells (data not shown). The MTT assay performed also shows that cells expressing the Dph2(C-) deletion mutant do not present any proliferation defect, their growth being comparable to that of wild-type CHO cells. Therefore, it shows that an EF-2 protein lacking diphthamide residue is not interfering with cell proliferation.

In order to ensure that none of the three Dph2 deletion mutants had Dph2 wild-type activity, stable RPE.33d cells expressing the three constructs were produced and assayed for DT resistance (by an MTT assay). All of the three Dph2 deletion mutants prevented DT sensitivity in RPE.33d cells whereas sensitivity to DT was present in RPE.33d cells having the complete Dph2 gene. These results show that the truncation of the C-terminal part of Dph2 confers a complete resistance to DT in a dominant manner.

Example 8

Figure 4:
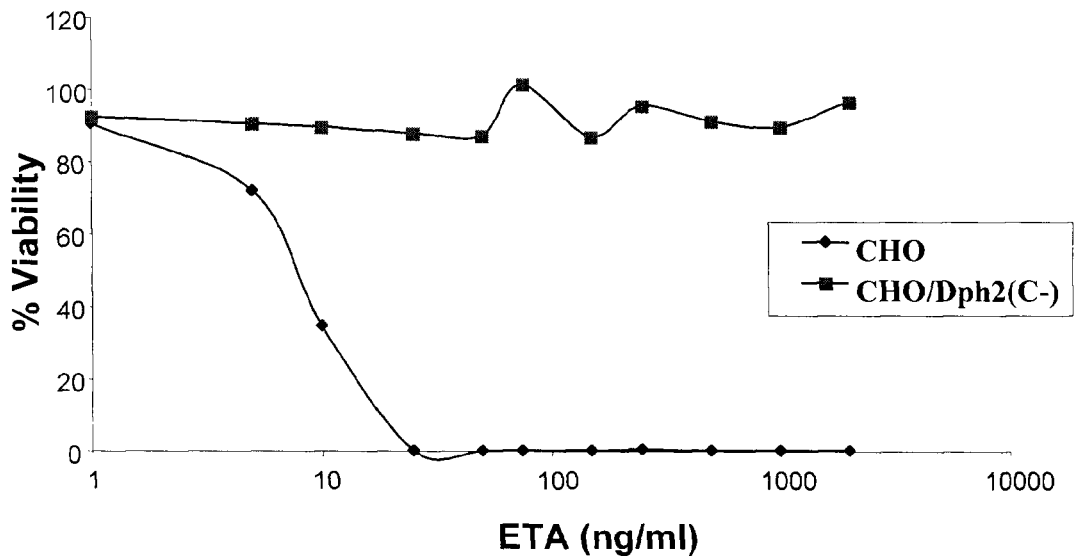
Figure 5:
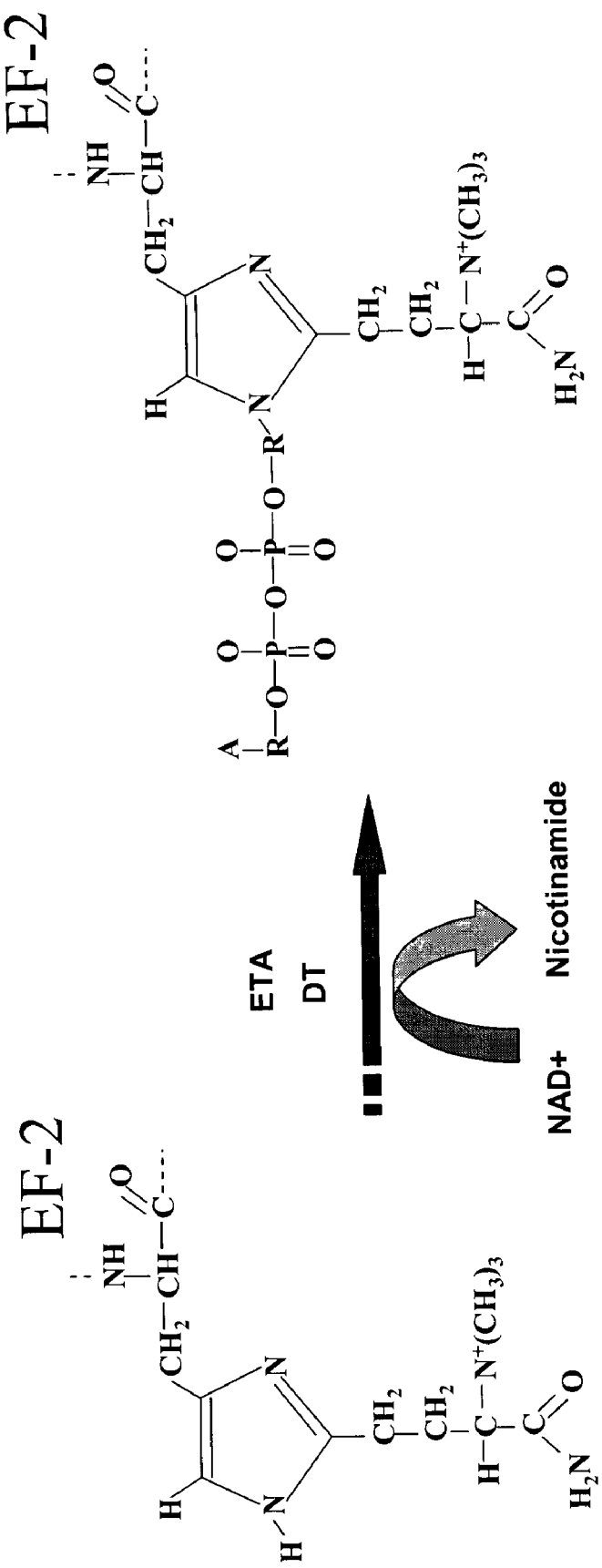
Figure 6:
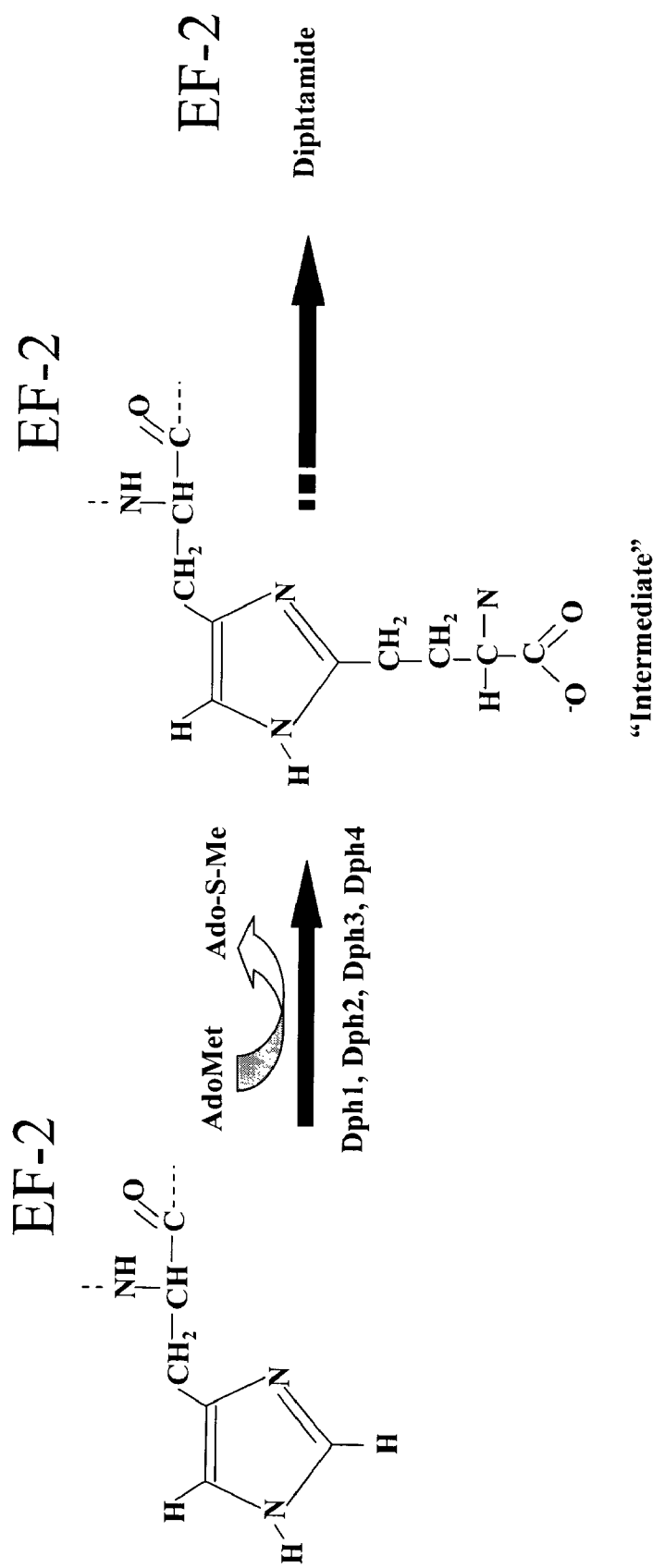

The C-Terminal Deletion in Dph2 Confers Resistance to ETA and Blocks Diphthamide Biosynthesis in Transfected Cells Without wishing to be bound by theory, it is suggested that the DT resistance of cells containing Dph2(C-) resides in the blockage of diphthamide biosynthesis. Thus, it is also suggested that other ADP-ribosylating toxins would not be able to ADP-ribosylate EF-2 in cells containing Dph2(C-). Since ETA ADP-ribosylates EF-2 on its diphthamide residue in the same way DT does, the C-terminal deletion of Dph2 should therefore render cells also resistant to ETA. To investigate this, an experiment similar to that presented in example 7 was performed to determine ETA resistance in the transfected cells. CHO cells stably expressing Dph2(C-) were shown to be completely resistant to ETA, at concentrations up to 2 ug/ml ETA, while a concentration of 25 ng/ml ETA was sufficient to kill wild-type CHO cells (FIG. 4).

Figure 7:
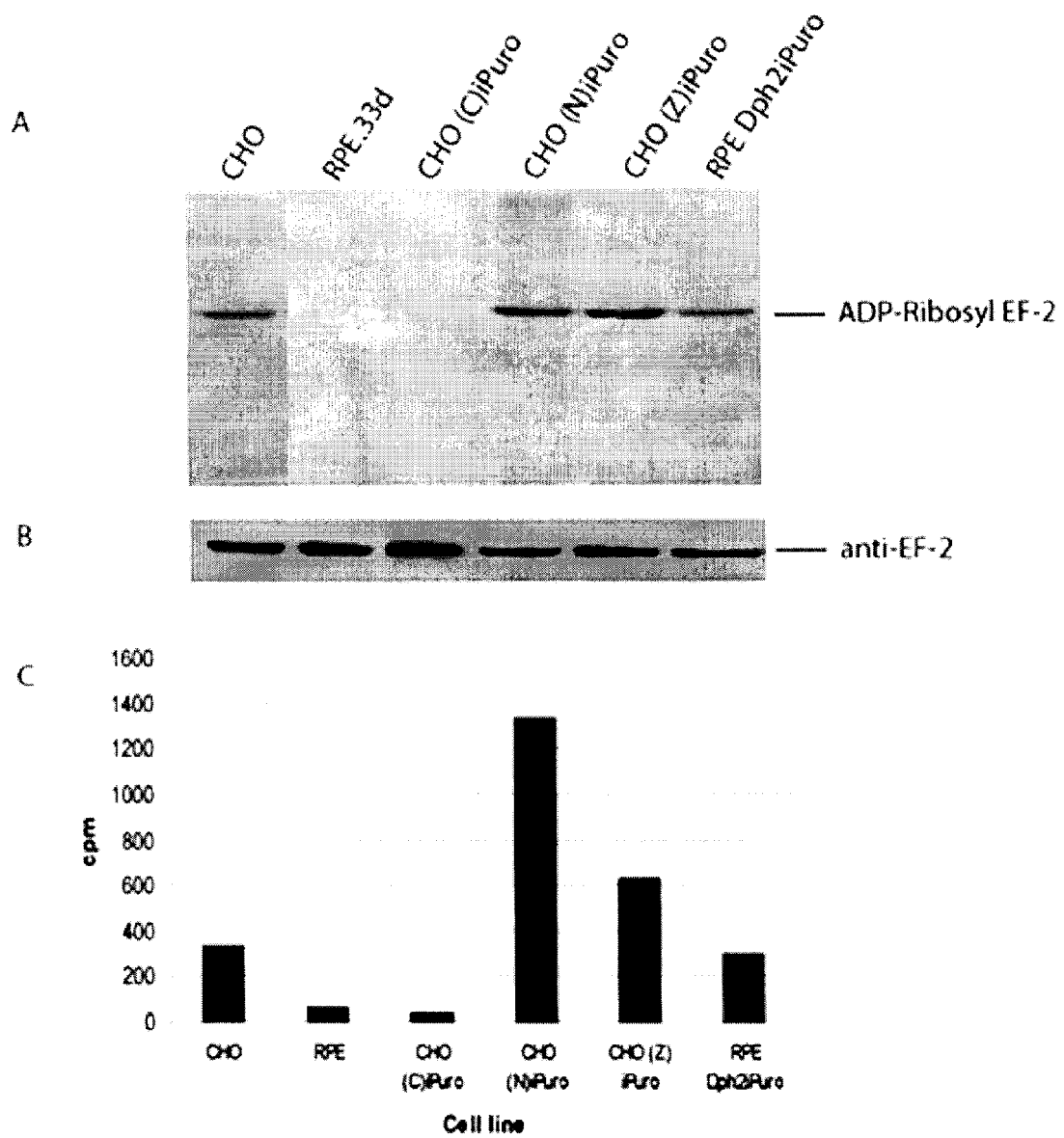

All of these results show that the ADP-ribosylating toxins can not perform their toxic activity on EF-2 in cell lines stably expressing the Dph2(C-) deletion mutant. The absence of diphthamide biosynthesis in cells transfected with Dph2(C-) is therefore probably the reason why this deletion mutant confers DT and ETA resistance. In order to further analyze the diphthamide biosynthesis, ADP-ribosylation of EF-2 was determined in the different stable cell lines (FIG. 7). Protein extracts from all CHO and REP.33d stable cell lines expressing the three different Dph2 deletion mutants were performed, and an assay where radiolabeled NAD[14] and fully nicked DT were added to the different cell extracts was performed. The EF-2 ADP-ribosylation was observable by autoradiography after the extracts were ran on an SDS-PAGE gel (FIG. 7A). An anti-EF-2 was used as a control (FIG. 7B). EF-2 was ADP-ribosylated in all cell extracts except in the RPE.33d cells and in the CHO cells stably transfected with Dph2(C-) (FIG. 7A, 7C). Without wishing to be bound by theory, the absence of ADP-ribosylation on EF-2 in stable CHO cells transfected with Dph2(C-) strongly suggests that diphthamide is not synthesized in those cells, and that this prevents DT from performing its toxic activity.

Example 9

Figure 9:
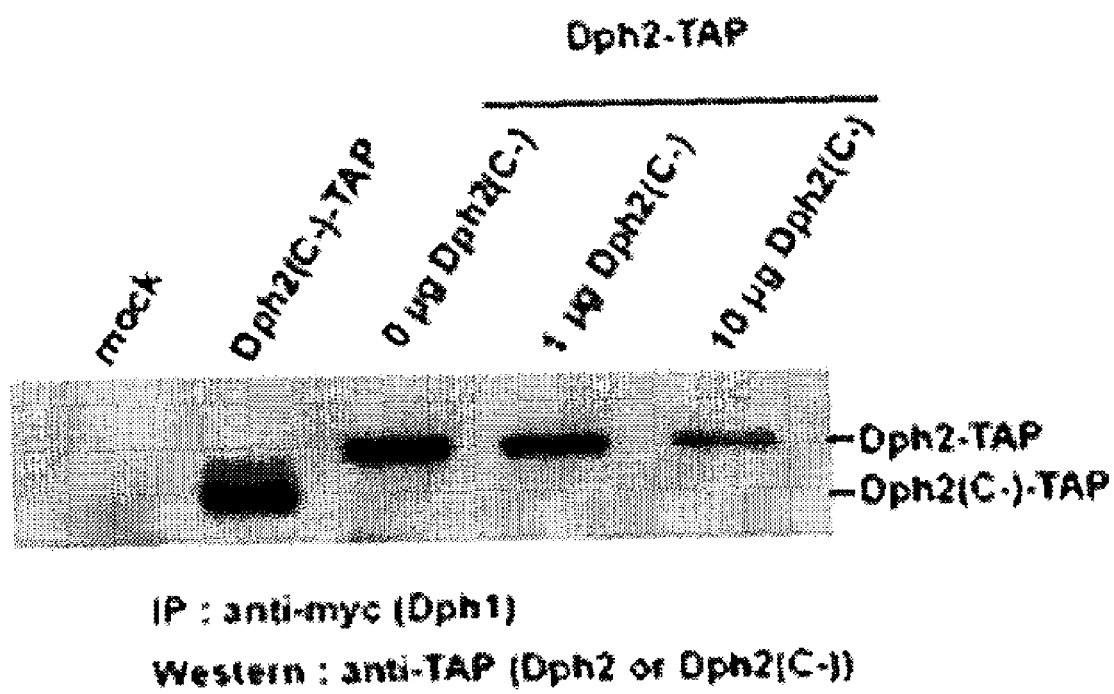

Dph2 Deletion Mutant Lacking a 98 Amino Acid C-Terminal Portion (Dph2(C-)) Still Associates with Dph1, but Prevent the Functionality of this Complex in Diphthamide Biosynthesis One explanation to the dominant negative phenotype of Dph2(C-) deletion mutant is that while Dph2(C-) still associates with Dph1 to form a protein complex, there is a blockade of the diphthamide biosynthesis capability of the protein complex. In order to investigate the association between Dph1 and Dph2(C-), immunoprecipitation assays were performed with a TAP-tagged Dph2(C-) and a Dph1 protein fused to a myc tag (FIG. 9). Functionality of the Dph2(C-) TAP and Dph2TAP constructs was first verified, because of the potential interference of the large TAP epitope with the complex function. ADP-ribosylation assays were performed in CHO cells expressing Dph2(C-), and in RPE.33d cells expressing a wild type Dph2 fused to the TAP tag, to ensure that both proteins maintained their known phenotypes (diphthamide biosynthesis for the wild type protein and inhibition of diphthamide biosynthesis for Dph2(C-)). The Dph2(C-) TAP construct was shown to block EF-2 ADP-ribosylation while the wild type Dph2TAP construct allowed for diphthamide formation in the RPE.33d cells. Those TAP constructs were also tested in MTT assays the same way it was done for the previous pMD2.KGiPURO constructs and showed that Dph2(C-)TAP still provided a complete resistance to DT. Furthermore, cotransfection of Dph2-TAP and Dph2(C-) expression plasmids in a 1:1 ratio (FIG. 9; lane 4) decreased the amount of Dph2-TAP recovered by immunoprecipitation with the anti-myc antibody (FIG. 9; lane 4 versus lane 3). With a 10-fold excess of the Dph2(C-) plasmid over the Dph2 plasmid, the band corresponding to Dph2-TAP on the Western blot was barely detected (FIG. 9; lane 5). These results clearly showed that Dph2(C-) binds to Dph1, and that it competes with Dph2.

While the invention has been described in connection with specific aspects thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. A method for inhibiting in vitro the formation of diphthamide in a human cell having wild-type dph-2 gene expressing wild-type Dph2(C-) protein, the method comprising: introducing a dominant negative Dph2(C-) protein in said cell, wherein said dominant negative Dph2(C-) protein is selected from the group consisting of: SEQ ID NO:2, SEQ ID NO:4, SEQ ID NO:6, SEQ ID NO:8 and SEQ ID NO:10, whereby said dominant negative protein Dph2(C-) inhibits said wild-type Dph2(C-) protein activity originally present in said human cell.

* * * * *